(12) United States Patent  
Ananny et al.

(10) Patent No.: US 9,137,309 B2  
(45) Date of Patent: Sep. 15, 2015

(54) CALIBRATION TECHNIQUES FOR ACTIVITY SENSING DEVICES

(75) Inventors: John Meron Ananny, San Francisco, CA (US); Nicholas Robert Kalayjian, San Carlos, CA (US)

(73) Assignee: Apple Inc., Cupertino, CA (US)

( * ) Notice: Subject to any disclaimer, the term of this patent is extended or adjusted under 35 U.S.C. 154(b) by 1509 days.

(21) Appl. No.: 11/585,721

(22) Filed: Oct. 23, 2006

(65) Prior Publication Data

US 2007/0270721 A1 Nov. 22, 2007

Related U.S. Application Data

(60) Provisional application No. 60/802,889, filed on May 22, 2006.

(51) Int. Cl.
*A61B 5/11* (2006.01)
*H04L 29/08* (2006.01)
(Continued)

(52) U.S. Cl.
CPC .......... *H04L 67/125* (2013.01); *A63B 24/0062* (2013.01); *A63B 69/0028* (2013.01); *G01C 22/006* (2013.01); *G01C 25/00* (2013.01); *G01P 21/00* (2013.01); *H04L 67/303* (2013.01); *A61B 5/11* (2013.01); *A63B 24/0075* (2013.01); *A63B 2024/0065* (2013.01); *A63B 2220/20* (2013.01); *A63B 2220/30* (2013.01); *A63B 2220/803* (2013.01); *A63B 2220/805* (2013.01);
(Continued)

(58) Field of Classification Search
CPC ....... A61B 5/11; A61B 5/1118; A61B 5/6801

USPC .................. 600/595, 300, 586, 587; 324/160; 702/160, 182
See application file for complete search history.

(56) References Cited

U.S. PATENT DOCUMENTS 3,612,265 A   10/1971   Dickerson
3,807,388 A    4/1974   Orr et al.
(Continued)

FOREIGN PATENT DOCUMENTS

DE   43 34 773 A1   4/1994
DE   44 45 023 A1   6/1996
(Continued)

OTHER PUBLICATIONS

International Search Report dated Dec. 6, 2007 in PCT Application No. PCT/US2007/010888.
(Continued)

*Primary Examiner* — Max Hindenburg
(74) *Attorney, Agent, or Firm* — Fish & Richardson P.C.

(57) ABSTRACT

Improved techniques and systems to calibrate an electronic device that is providing activity sensing are disclosed. The activity being sensed can, for example, correspond to walking or running by a user. In one embodiment, calibration can be performed by a portable electronic device so that activity data it receives from a remote sensor device can be more accurately processed. The improved techniques and systems to calibrate can be used to monitor, process, present and manage data captured by a remote sensor. The portable electronic device can also offer a convenient user interface that can be visual and/or audio based, customized to a particular application, user-friendly and/or dynamic. The portable electronic device can pertain to a portable media player and thus also provide media playback.

13 Claims, 14 Drawing Sheets

(51) Int. Cl.
 *A63B 24/00* (2006.01)
 *A63B 69/00* (2006.01)
 *G01C 22/00* (2006.01)
 *G01C 25/00* (2006.01)
 *G01P 21/00* (2006.01)

(52) U.S. Cl.
 CPC ......... *A63B2225/02* (2013.01); *A63B 2225/20* (2013.01); *A63B 2225/50* (2013.01); *A63B 2225/54* (2013.01); *A63B 2230/06* (2013.01)

(56) References Cited

U.S. PATENT DOCUMENTS

| | | | |
|---|---|---|---|
| 3,918,058 A | 11/1975 | Noyori et al. |
| 3,958,459 A | 5/1976 | Shimomura |
| 3,978,725 A | 9/1976 | Hadtke |
| 4,089,057 A | 5/1978 | Eriksson |
| 4,090,216 A | 5/1978 | Constable |
| 4,101,873 A | 7/1978 | Anderson et al. |
| 4,114,450 A | 9/1978 | Shulmann et al. |
| 4,195,642 A | 4/1980 | Price et al. |
| 4,210,024 A | 7/1980 | Ishiwatari et al. |
| 4,223,211 A | 9/1980 | Allsen et al. |
| 4,248,244 A | 2/1981 | Charnitski et al. |
| 4,317,126 A | 2/1982 | Gragg, Jr. |
| 4,371,188 A | 2/1983 | Hull |
| 4,371,945 A | 2/1983 | Karr et al. |
| 4,375,674 A | 3/1983 | Thornton |
| 4,386,345 A | 5/1983 | Narveson et al. |
| 4,423,630 A | 1/1984 | Morrison |
| 4,434,801 A | 3/1984 | Jiminez et al. |
| 4,451,849 A | 5/1984 | Fuhrer |
| 4,516,110 A | 5/1985 | Overmyer |
| 4,516,865 A | 5/1985 | Hideo |
| 4,578,769 A | 3/1986 | Frederick |
| 4,589,022 A | 5/1986 | Prince et al. |
| 4,625,733 A | 12/1986 | Saynajakangas |
| 4,694,694 A | 9/1987 | Vlakancic et al. |
| 4,699,379 A | 10/1987 | Chateau et al. |
| 4,703,445 A | 10/1987 | Dassler |
| 4,720,093 A | 1/1988 | Del Mar |
| 4,722,222 A | 2/1988 | Purdy et al. |
| 4,736,312 A | 4/1988 | Dassler et al. |
| 4,745,564 A | 5/1988 | Tennes et al. |
| 4,757,453 A | 7/1988 | Nasiff |
| 4,757,714 A | 7/1988 | Purdy et al. |
| 4,759,219 A | 7/1988 | Cobb et al. |
| 4,763,275 A | 8/1988 | Carlin |
| 4,763,284 A | 8/1988 | Carlin |
| 4,763,287 A | 8/1988 | Gerhaeuser et al. |
| 4,771,394 A | 9/1988 | Cavanagh |
| 4,774,679 A | 9/1988 | Carlin |
| 4,775,948 A | 10/1988 | Dial et al. |
| 4,780,837 A | 10/1988 | Namekawa |
| 4,821,218 A | 4/1989 | Potsch |
| 4,822,042 A | 4/1989 | Landsman |
| 4,824,107 A | 4/1989 | French |
| 4,829,812 A | 5/1989 | Parks et al. |
| 4,830,021 A | 5/1989 | Thornton |
| 4,862,394 A | 8/1989 | Thompson et al. |
| 4,862,395 A | 8/1989 | Fey et al. |
| 4,873,867 A | 10/1989 | McPherson et al. |
| 4,876,500 A | 10/1989 | Wu |
| 4,883,271 A | 11/1989 | French |
| 4,903,212 A | 2/1990 | Yokouchi et al. |
| 4,908,523 A | 3/1990 | Snowden et al. |
| 4,928,307 A | 5/1990 | Lynn |
| 4,935,887 A | 6/1990 | Abdalah et al. |
| 4,951,171 A | 8/1990 | Tran et al. |
| 4,955,980 A | 9/1990 | Masuo |
| 5,033,013 A | 7/1991 | Kato et al. |
| 5,036,467 A | 7/1991 | Blackburn et al. |
| 5,056,783 A | 10/1991 | Matcovich et al. |
| 5,067,081 A | 11/1991 | Person |
| 5,088,836 A | 2/1992 | Yameda et al. |
| 5,117,444 A | 5/1992 | Sutton et al. |
| 5,144,226 A | 9/1992 | Rapp |
| 5,148,002 A | 9/1992 | Kuo et al. |
| 5,150,310 A | 9/1992 | Greenspun et al. |
| 5,162,828 A | 11/1992 | Furness et al. |
| 5,181,181 A | 1/1993 | Glynn |
| 5,200,827 A | 4/1993 | Hanson et al. |
| 5,243,993 A | 9/1993 | Alexander et al. |
| 5,258,927 A | 11/1993 | Havriluk et al. |
| 5,295,085 A | 3/1994 | Hoffacker |
| 5,316,249 A | 5/1994 | Anderson |
| 5,324,038 A | 6/1994 | Sasser |
| 5,335,664 A | 8/1994 | Nagashima |
| 5,339,699 A | 8/1994 | Carignan |
| 5,343,445 A | 8/1994 | Cherdak |
| 5,348,519 A | 9/1994 | Prince et al. |
| 5,382,972 A | 1/1995 | Kannes |
| 5,396,429 A | 3/1995 | Hanchett |
| 5,406,305 A | 4/1995 | Shimomura et al. |
| 5,420,828 A | 5/1995 | Geiger |
| 5,426,595 A | 6/1995 | Picard |
| 5,436,838 A | 7/1995 | Miyamori |
| 5,446,775 A | 8/1995 | Wright et al. |
| 5,450,329 A | 9/1995 | Tanner |
| 5,452,269 A | 9/1995 | Cherdak |
| 5,471,405 A | 11/1995 | Marsh |
| 5,475,725 A | 12/1995 | Nakamura |
| 5,476,427 A | 12/1995 | Fujima |
| 5,478,006 A | 12/1995 | Taguchi |
| 5,485,402 A | 1/1996 | Smith et al. |
| 5,486,815 A | 1/1996 | Wagner |
| 5,509,082 A | 4/1996 | Toyama et al. |
| 5,513,854 A | 5/1996 | Daver |
| 5,524,637 A | 6/1996 | Erickson |
| 5,526,326 A | 6/1996 | Fekete et al. |
| 5,528,228 A | 6/1996 | Wilk |
| 5,539,336 A | 7/1996 | Nguyen et al. |
| 5,541,604 A | 7/1996 | Meier |
| 5,546,307 A | 8/1996 | Mazur et al. |
| 5,546,974 A | 8/1996 | Bireley |
| 5,559,945 A | 9/1996 | Beaudet et al. |
| 5,564,698 A | 10/1996 | Honey et al. |
| 5,574,669 A | 11/1996 | Marshall |
| 5,583,776 A | 12/1996 | Levi et al. |
| 5,583,993 A | 12/1996 | Foster et al. |
| 5,590,908 A | 1/1997 | Carr |
| 5,592,401 A | 1/1997 | Kramer |
| 5,605,336 A | 2/1997 | Gaoiran et al. |
| 5,608,698 A | 3/1997 | Yamanoi et al. |
| 5,615,132 A | 3/1997 | Horton et al. |
| 5,616,876 A | 4/1997 | Cluts |
| 5,617,084 A | 4/1997 | Sears |
| 5,617,386 A | 4/1997 | Choi |
| 5,618,995 A | 4/1997 | Otto et al. |
| 5,627,548 A | 5/1997 | Woo et al. |
| 5,629,131 A | 5/1997 | De Keyzer et al. |
| 5,633,070 A | 5/1997 | Murayama et al. |
| 5,636,146 A | 6/1997 | Flentov et al. |
| 5,646,857 A | 7/1997 | McBurney et al. |
| 5,670,985 A | 9/1997 | Cappels, Sr. et al. |
| 5,671,010 A | 9/1997 | Shimbo et al. |
| 5,671,162 A | 9/1997 | Werbin |
| 5,673,691 A | 10/1997 | Abrams et al. |
| 5,680,102 A | 10/1997 | Xydis |
| 5,684,513 A | 11/1997 | Decker |
| 5,688,183 A | 11/1997 | Sabatino et al. |
| 5,690,119 A | 11/1997 | Rytky et al. |
| 5,690,591 A | 11/1997 | Kenmochi et al. |
| 5,690,773 A | 11/1997 | Fidalgo et al. |
| 5,694,340 A | 12/1997 | Kim |
| 5,701,257 A | 12/1997 | Miura et al. |
| 5,710,922 A | 1/1998 | Alley et al. |
| 5,712,638 A | 1/1998 | Issa |
| 5,712,949 A | 1/1998 | Kato et al. |
| 5,720,200 A | 2/1998 | Anderson et al. |
| 5,721,539 A | 2/1998 | Goetzl |
| 5,721,949 A | 2/1998 | Smith et al. |
| 5,723,786 A | 3/1998 | Klapman |
| 5,724,265 A | 3/1998 | Hutchings |

(56) References Cited

U.S. PATENT DOCUMENTS

| | | |
|---|---|---|
| 5,726,672 A | 3/1998 | Hernandez et al. |
| 5,734,337 A | 3/1998 | Kupersmit |
| 5,738,104 A | 4/1998 | Lo et al. |
| 5,739,451 A | 4/1998 | Winksy et al. |
| 5,740,143 A | 4/1998 | Suetomi |
| 5,743,269 A | 4/1998 | Okigami et al. |
| 5,745,037 A | 4/1998 | Guthrie et al. |
| 5,749,615 A | 5/1998 | Itson |
| 5,761,096 A | 6/1998 | Zakutin |
| 5,771,485 A | 6/1998 | Echigo |
| 5,779,576 A | 7/1998 | Smith, III et al. |
| 5,781,155 A | 7/1998 | Woo et al. |
| 5,790,477 A | 8/1998 | Hauke |
| 5,807,284 A | 9/1998 | Foxlin |
| 5,812,056 A | 9/1998 | Law |
| 5,815,225 A | 9/1998 | Nelson |
| 5,822,288 A | 10/1998 | Shinada |
| 5,835,721 A | 11/1998 | Donahue et al. |
| 5,835,732 A | 11/1998 | Kikinis et al. |
| 5,862,803 A | 1/1999 | Besson et al. |
| 5,864,868 A | 1/1999 | Contois |
| 5,870,710 A | 2/1999 | Ozawa et al. |
| 5,886,739 A | 3/1999 | Winningstad |
| 5,891,042 A | 4/1999 | Sham et al. |
| 5,895,073 A | 4/1999 | Moore |
| 5,897,457 A | 4/1999 | Mackovjak |
| 5,899,963 A | 5/1999 | Hutchings |
| 5,901,303 A | 5/1999 | Chew |
| 5,905,460 A | 5/1999 | Odagiri et al. |
| 5,918,281 A | 6/1999 | Nabulsi |
| 5,918,303 A | 6/1999 | Yamaura et al. |
| 5,920,728 A | 7/1999 | Hallowell et al. |
| 5,923,757 A | 7/1999 | Hocker et al. |
| 5,925,001 A | 7/1999 | Hoyt et al. |
| 5,929,335 A | 7/1999 | Carter |
| 5,930,741 A | 7/1999 | Kramer |
| 5,936,523 A | 8/1999 | West |
| 5,946,643 A | 8/1999 | Zakutin |
| 5,947,917 A | 9/1999 | Carte et al. |
| 5,952,992 A | 9/1999 | Helms |
| 5,955,667 A | 9/1999 | Fyfe |
| 5,959,568 A | 9/1999 | Wooley |
| 5,960,380 A | 9/1999 | Flentov et al. |
| 5,963,523 A | 10/1999 | Kayama et al. |
| 5,963,891 A | 10/1999 | Walker et al. |
| 5,976,083 A | 11/1999 | Richardson et al. |
| 5,977,877 A | 11/1999 | McCulloch et al. |
| 5,978,972 A | 11/1999 | Stewart et al. |
| 5,984,842 A | 11/1999 | Chu |
| 6,002,982 A | 12/1999 | Fry |
| 6,006,274 A | 12/1999 | Hawkins et al. |
| 6,009,237 A | 12/1999 | Hirabayashi et al. |
| 6,009,629 A | 1/2000 | Gnepf et al. |
| 6,011,491 A | 1/2000 | Goetzi |
| 6,011,585 A | 1/2000 | Anderson |
| 6,013,007 A | 1/2000 | Root et al. |
| 6,018,677 A | 1/2000 | Vidrine et al. |
| 6,018,705 A | 1/2000 | Gaudet et al. |
| 6,020,851 A | 2/2000 | Busack |
| 6,028,617 A | 2/2000 | Sawano et al. |
| 6,028,625 A | 2/2000 | Cannon |
| 6,028,627 A | 2/2000 | Helmsderfer |
| 6,032,084 A | 2/2000 | Anderson et al. |
| 6,032,108 A | 2/2000 | Seiple et al. |
| 6,032,530 A | 3/2000 | Hock |
| 6,041,023 A | 3/2000 | Lakhansingh |
| 6,043,747 A | 3/2000 | Altenhofen |
| 6,045,364 A | 4/2000 | Dugan et al. |
| 6,052,654 A | 4/2000 | Gaudet et al. |
| 6,057,756 A | 5/2000 | Engellener |
| 6,059,576 A | 5/2000 | Brann |
| 6,073,086 A | 6/2000 | Marinelli |
| 6,074,271 A | 6/2000 | Derrah |
| 6,075,443 A | 6/2000 | Schepps et al. |
| 6,091,342 A | 7/2000 | Janesch et al. |
| 6,108,426 A | 8/2000 | Stortz |
| 6,111,541 A | 8/2000 | Karmel |
| 6,111,571 A | 8/2000 | Summers |
| 6,122,340 A | 9/2000 | Darley et al. |
| 6,122,959 A | 9/2000 | Hoshal et al. |
| 6,122,960 A | 9/2000 | Hutchings |
| 6,125,686 A | 10/2000 | Haan et al. |
| 6,127,931 A | 10/2000 | Mohr |
| 6,145,389 A | 11/2000 | Ebeling et al. |
| 6,148,271 A | 11/2000 | Marinelli |
| 6,151,647 A | 11/2000 | Sarat |
| 6,157,898 A | 12/2000 | Marinelli |
| 6,160,254 A | 12/2000 | Zimmerman et al. |
| 6,161,944 A | 12/2000 | Leman |
| 6,163,021 A | 12/2000 | Mickelson |
| 6,167,356 A | 12/2000 | Squadron et al. |
| 6,172,948 B1 | 1/2001 | Keller et al. |
| 6,179,432 B1 | 1/2001 | Zhang et al. |
| 6,183,425 B1 | 2/2001 | Whalen et al. |
| 6,191,939 B1 | 2/2001 | Burnett |
| 6,196,932 B1 | 3/2001 | Marsh et al. |
| 6,204,813 B1 | 3/2001 | Wadell et al. |
| 6,208,044 B1 | 3/2001 | Viswanadham et al. |
| 6,216,131 B1 | 4/2001 | Liu et al. |
| 6,217,183 B1 | 4/2001 | Shipman |
| 6,226,622 B1 | 5/2001 | Dabbiere |
| 6,238,338 B1 | 5/2001 | DeLuca et al. |
| 6,245,002 B1 | 6/2001 | Belikov |
| 6,248,946 B1 | 6/2001 | Dwek |
| 6,249,487 B1 | 6/2001 | Yano et al. |
| 6,254,513 B1 | 7/2001 | Takenaka et al. |
| 6,263,279 B1 | 7/2001 | Bianco et al. |
| 6,266,623 B1 | 7/2001 | Vock et al. |
| 6,295,541 B1 | 9/2001 | Bodnar et al. |
| 6,298,314 B1 | 10/2001 | Blackadar et al. |
| 6,305,221 B1 | 10/2001 | Hutchings |
| 6,332,175 B1 | 12/2001 | Birrell et al. |
| 6,336,365 B1 | 1/2002 | Blackadar et al. |
| 6,336,727 B1 | 1/2002 | Kim |
| 6,341,316 B1 | 1/2002 | Kloba et al. |
| 6,356,856 B1 | 3/2002 | Damen et al. |
| 6,357,147 B1 | 3/2002 | Darley et al. |
| 6,360,597 B1 | 3/2002 | Hubbard, Jr. |
| 6,377,530 B1 | 4/2002 | Burrows |
| 6,380,597 B1 | 4/2002 | Gudesen et al. |
| 6,385,473 B1 | 5/2002 | Haines et al. |
| 6,436,052 B1 | 8/2002 | Nikolic et al. |
| 6,441,747 B1 | 8/2002 | Khair et al. |
| 6,452,610 B1 | 9/2002 | Reinhardt et al. |
| 6,456,261 B1 | 9/2002 | Zhang |
| 6,459,881 B1 | 10/2002 | Hoder et al. |
| 6,467,924 B2 | 10/2002 | Shipman |
| 6,493,652 B1 * | 12/2002 | Ohlenbusch et al. ......... 702/160 |
| 6,498,994 B2 | 12/2002 | Vock et al. |
| 6,501,393 B1 | 12/2002 | Richards et al. |
| 6,504,483 B1 | 1/2003 | Richards et al. |
| 6,516,284 B2 | 2/2003 | Flentov et al. |
| 6,527,711 B1 | 3/2003 | Stivoric |
| 6,529,131 B2 | 3/2003 | Wentworth |
| 6,531,982 B1 | 3/2003 | White et al. |
| 6,536,139 B2 | 3/2003 | Darley et al. |
| 6,539,336 B1 | 3/2003 | Vock et al. |
| 6,549,497 B2 | 4/2003 | Miyamoto et al. |
| 6,560,903 B1 | 5/2003 | Darley |
| 6,563,417 B1 | 5/2003 | Shaw |
| 6,570,526 B1 | 5/2003 | Noller et al. |
| 6,587,403 B1 | 7/2003 | Keller et al. |
| 6,587,404 B1 | 7/2003 | Keller et al. |
| 6,595,929 B2 | 7/2003 | Stivoric |
| 6,600,418 B2 | 7/2003 | Francis et al. |
| 6,605,038 B1 | 8/2003 | Teller et al. |
| 6,611,782 B1 | 8/2003 | Wooster |
| 6,611,789 B1 | 8/2003 | Darley |
| 6,617,962 B1 | 9/2003 | Horwitz et al. |
| 6,619,835 B2 | 9/2003 | Kita |
| 6,621,768 B1 | 9/2003 | Keller et al. |
| 6,623,427 B2 | 9/2003 | Mandigo |
| 6,633,743 B1 | 10/2003 | Berlinsky |
| 6,643,608 B1 | 11/2003 | Hershey et al. |

(56) References Cited

U.S. PATENT DOCUMENTS

| | | |
|---|---|---|
| 6,714,121 B1 | 3/2004 | Moore |
| 6,731,312 B2 | 5/2004 | Robbin |
| 6,735,630 B1 | 5/2004 | Gelvin et al. |
| 6,748,902 B1 | 6/2004 | Boesch et al. |
| 6,760,536 B1 | 7/2004 | Amir et al. |
| 6,762,741 B2 | 7/2004 | Weindorf |
| 6,772,331 B1 | 8/2004 | Hind et al. |
| 6,794,566 B2 | 9/2004 | Pachet |
| 6,799,226 B1 | 9/2004 | Robbin et al. |
| 6,801,964 B1 | 10/2004 | Mahdavi |
| 6,813,586 B1 | 11/2004 | Vock et al. |
| 6,825,777 B2 | 11/2004 | Vock et al. |
| 6,837,827 B1 | 1/2005 | Lee et al. |
| 6,856,934 B2 | 2/2005 | Vock et al. |
| 6,870,529 B1 | 3/2005 | Davis |
| 6,871,063 B1 | 3/2005 | Schiffer |
| 6,876,947 B1 | 4/2005 | Darley et al. |
| 6,882,955 B1 | 4/2005 | Ohlenbusch et al. |
| 6,883,694 B2 | 4/2005 | Abelow |
| 6,885,971 B2 | 4/2005 | Vock et al. |
| 6,898,550 B1 | 5/2005 | Blackadar et al. |
| 6,900,732 B2 | 5/2005 | Richards |
| 6,911,971 B2 | 6/2005 | Suzuki et al. |
| 6,914,551 B2 | 7/2005 | Vidal |
| 6,918,677 B2 | 7/2005 | Shipman |
| 6,934,812 B1 | 8/2005 | Robbin et al. |
| 6,950,087 B2 | 9/2005 | Knox et al. |
| 6,959,259 B2 | 10/2005 | Vock et al. |
| 7,009,517 B2 | 3/2006 | Wood |
| 7,042,360 B2 | 5/2006 | Light et al. |
| 7,046,230 B2 | 5/2006 | Zadesky |
| 7,054,784 B2 | 5/2006 | Flentov et al. |
| 7,062,225 B2 | 6/2006 | White |
| 7,064,669 B2 | 6/2006 | Light et al. |
| 7,072,789 B2 | 7/2006 | Vock et al. |
| 7,084,856 B2 | 8/2006 | Huppi |
| 7,084,921 B1 | 8/2006 | Ogawa |
| 7,092,846 B2 | 8/2006 | Vock et al. |
| 7,146,437 B2 | 12/2006 | Robbin et al. |
| 7,174,130 B2 | 2/2007 | Kurisko et al. |
| 7,174,277 B2 | 2/2007 | Vock et al. |
| 7,234,026 B2 | 6/2007 | Robbin et al. |
| 7,254,516 B2 | 8/2007 | Case et al. |
| 7,292,588 B2 | 11/2007 | Milley et al. |
| 7,296,107 B2 | 11/2007 | Lunsford et al. |
| 7,450,084 B2 | 11/2008 | Fuller et al. |
| 7,559,877 B2 * | 7/2009 | Parks et al. ............ 482/8 |
| 7,600,227 B2 | 10/2009 | Brockway et al. |
| 7,647,129 B1 | 1/2010 | Griffin, Jr. |
| 7,653,928 B2 | 1/2010 | Almstrand et al. |
| 7,783,065 B2 | 8/2010 | Navid |
| 2001/0022828 A1 | 9/2001 | Pyles |
| 2001/0033244 A1 | 10/2001 | Harris et al. |
| 2001/0041021 A1 | 11/2001 | Boyle et al. |
| 2001/0042107 A1 | 11/2001 | Palm |
| 2001/0049890 A1 | 12/2001 | Hirsch et al. |
| 2002/0002413 A1 | 1/2002 | Tokue |
| 2002/0013784 A1 | 1/2002 | Swanson |
| 2002/0022551 A1 | 2/2002 | Watterson et al. |
| 2002/0032911 A1 | 3/2002 | Tanaka et al. |
| 2002/0045961 A1 | 4/2002 | Gibbs et al. |
| 2002/0046315 A1 | 4/2002 | Miller et al. |
| 2002/0055934 A1 | 5/2002 | Lipscomb et al. |
| 2002/0090912 A1 | 7/2002 | Cannon et al. |
| 2002/0116082 A1 | 8/2002 | Gudorf |
| 2002/0144024 A1 | 10/2002 | Kumpf et al. |
| 2002/0152045 A1 | 10/2002 | Dowling et al. |
| 2002/0161865 A1 | 10/2002 | Nguyen |
| 2002/0173273 A1 | 11/2002 | Spurgat et al. |
| 2002/0189426 A1 | 12/2002 | Hirade et al. |
| 2003/0016844 A1 | 1/2003 | Numaoka |
| 2003/0037254 A1 | 2/2003 | Fischer et al. |
| 2003/0046434 A1 | 3/2003 | Flanagin et al. |
| 2003/0065805 A1 | 4/2003 | Barnes |
| 2003/0074457 A1 | 4/2003 | Kluth |
| 2003/0076301 A1 | 4/2003 | Tsuk et al. |
| 2003/0079038 A1 | 4/2003 | Robbin et al. |
| 2003/0095096 A1 | 5/2003 | Robbin et al. |
| 2003/0097379 A1 | 5/2003 | Ireton |
| 2003/0133694 A1 | 7/2003 | Yeo |
| 2003/0149875 A1 | 8/2003 | Hosaka |
| 2003/0163287 A1 | 8/2003 | Volk et al. |
| 2003/0167318 A1 | 9/2003 | Robbin et al. |
| 2003/0229490 A1 | 12/2003 | Etter |
| 2004/0001395 A1 | 1/2004 | Keller et al. |
| 2004/0001396 A1 | 1/2004 | Keller et al. |
| 2004/0012556 A1 | 1/2004 | Yong et al. |
| 2004/0055446 A1 | 3/2004 | Robbin et al. |
| 2004/0069122 A1 | 4/2004 | Wilson |
| 2004/0076086 A1 | 4/2004 | Keller |
| 2004/0086120 A1 | 5/2004 | Akins, III et al. |
| 2004/0094018 A1 | 5/2004 | Ueshima et al. |
| 2004/0104845 A1 | 6/2004 | McCarthy |
| 2004/0198436 A1 | 10/2004 | Alden |
| 2004/0224638 A1 | 11/2004 | Fadell et al. |
| 2004/0253983 A1 | 12/2004 | Vanhatalo et al. |
| 2004/0267825 A1 | 12/2004 | Novak et al. |
| 2005/0015254 A1 | 1/2005 | Beaman |
| 2005/0027910 A1 | 2/2005 | Barrett, Jr. et al. |
| 2005/0080566 A1 | 4/2005 | Vock et al. |
| 2005/0088275 A1 | 4/2005 | Valoteau et al. |
| 2005/0152294 A1 | 7/2005 | Yu et al. |
| 2005/0166153 A1 | 7/2005 | Eytchison et al. |
| 2005/0177929 A1 | 8/2005 | Greenwald et al. |
| 2005/0245839 A1 | 11/2005 | Stivoric et al. |
| 2005/0262557 A1 | 11/2005 | Fellenstein et al. |
| 2005/0266798 A1 | 12/2005 | Moloney et al. |
| 2005/0266961 A1 | 12/2005 | Shum et al. |
| 2005/0275541 A1 | 12/2005 | Sengupta et al. |
| 2006/0013414 A1 | 1/2006 | Shih |
| 2006/0068760 A1 | 3/2006 | Hameed et al. |
| 2006/0094402 A1 | 5/2006 | Kim |
| 2006/0097847 A1 | 5/2006 | Bervoets et al. |
| 2006/0123138 A1 | 6/2006 | Perdomo et al. |
| 2006/0135064 A1 | 6/2006 | Cho et al. |
| 2006/0143455 A1 | 6/2006 | Gitzinger |
| 2006/0152377 A1 | 7/2006 | Beebe et al. |
| 2006/0190577 A1 | 8/2006 | Yamada |
| 2006/0221788 A1 | 10/2006 | Lindahl et al. |
| 2006/0265503 A1 | 11/2006 | Jones et al. |
| 2006/0265661 A1 | 11/2006 | Ball |
| 2007/0011919 A1 | 1/2007 | Case, Jr. |
| 2007/0021269 A1 | 1/2007 | Shum |
| 2007/0028009 A1 | 2/2007 | Robbin et al. |
| 2007/0032195 A1 | 2/2007 | Kurisko et al. |
| 2007/0124679 A1 | 5/2007 | Jeong et al. |
| 2008/0016537 A1 | 1/2008 | Little et al. |
| 2008/0125288 A1 | 5/2008 | Case |
| 2008/0262392 A1 | 10/2008 | Ananny et al. |

FOREIGN PATENT DOCUMENTS

| | | |
|---|---|---|
| DE | 10325805 | 1/2005 |
| EP | 0 127 139 | 5/1984 |
| EP | 0336782 A2 | 10/1989 |
| EP | 0578604 | 1/1994 |
| EP | 0 757 437 | 2/1997 |
| EP | 0 863 469 | 9/1998 |
| EP | 0 917 077 | 5/1999 |
| EP | 0917893 B1 | 5/1999 |
| EP | 0 982 732 | 3/2000 |
| EP | 1 028 425 | 8/2000 |
| EP | 1028426 A2 | 8/2000 |
| EP | 1 076 302 | 2/2001 |
| EP | 1289197 | 3/2003 |
| EP | 1 455 477 | 9/2004 |
| EP | 1536612 | 6/2005 |
| EP | 1566948 | 8/2005 |
| GB | 1567238 | 5/1980 |
| GB | 2137363 | 10/1984 |
| GB | 2384399 | 7/2003 |
| JP | 59-023610 | 2/1984 |
| JP | 03-152469 | 6/1991 |
| JP | 2000122044 | 4/2000 |

(56) References Cited

FOREIGN PATENT DOCUMENTS

| | | |
|---|---|---|
| JP | 2000-224099 | 8/2000 |
| JP | 2000-299834 | 10/2000 |
| JP | 2001-312338 | 11/2001 |
| JP | 2001321202 | 11/2001 |
| JP | 2002-076977 | 3/2002 |
| JP | 2002101908 | 4/2002 |
| WO | WO 01/33569 | 6/1995 |
| WO | WO 95/16950 | 6/1995 |
| WO | WO 98/17032 | 4/1998 |
| WO | WO 98/06466 | 12/1998 |
| WO | WO 98/54581 | 12/1998 |
| WO | WO 00/22820 | 4/2000 |
| WO | WO 00/51259 | 8/2000 |
| WO | WO 00/78170 | 12/2000 |
| WO | WO 01/01706 A1 | 4/2001 |
| WO | WO 01/65413 | 9/2001 |
| WO | WO 01/67753 | 9/2001 |
| WO | WO 02/25610 | 3/2002 |
| WO | WO 03/023786 | 3/2003 |
| WO | WO 03/067202 | 8/2003 |
| WO | 2004/061850 A1 | 7/2004 |
| WO | WO 2004/055637 | 7/2004 |
| WO | WO2004/084413 A2 | 9/2004 |
| WO | WO 2005/031737 | 4/2005 |
| WO | WO 2005/048644 | 5/2005 |
| WO | WO 2005/008505 | 7/2005 |
| WO | WO 2005/109781 | 11/2005 |
| WO | WO 2006071364 | 6/2006 |
| WO | WO 2006/094380 | 9/2006 |
| WO | WO 2007/022421 | 2/2007 |

OTHER PUBLICATIONS

Written Opinion dated Dec. 6, 2007 in PCT Application No. PCT/US2007/010888.
Apple iTunes Smart Playlists, downloaded Apr. 5, 2005 from http://web.archive.org/web/20031002011316/www.apple.com/itunes/smartplaylists . . . pp. 1-2.
Hart-Daves, Guy, "How to Do Everything with Your IPod & Mini IPod Mini", 2004, McGraw-Hill Professional, p. 33.
International Search Report in Patent Application No. PCT/US2006/048738 dated Jan. 29, 2008.
International Search Report in Patent Application No. PCT/US2007/077020 dated Jan. 28, 2008.
International Search Report in Patent Application No. PCT/US2007/076889 dated Jan. 28, 2008.
iTunes, Wikipedia, the free encyclopedia; downloaded on Oct. 5, 2005, pp. 1-6.
Nutzel et al., "Sharing Systems for Future HiFi Systems", The Computer Society, Jun. 2004.
Office Action Dated Feb. 1, 2008 in U.S. Appl. No. 11/327,544.
Office Action Dated Feb. 4, 2008 in US Appl. No. 11/566,072.
Written Opinion in Patent Application No. PCT/US2006/048738 dated Jan. 29, 2008.
Written Opinion in Patent Application No. PCT/US2007/076889 dated Jan. 28, 2008.
Written Opinion in Patent Application No. PCT/US2007/077020 dated Jan. 28, 2008.
U.S. Appl. No. 10/125,893, filed Apr. 18, 2002 and titled "Power Adapters for Powering and/or Charging Peripheral Devices.".
International Search Report dated Nov. 24, 2006 in PCT Application No. PCT/US2005/046797.
International Search Report dated Jul. 10, 2007 in corresponding application No. PCT/US2006/048738.
Written Opinion of the International Searching Authority dated Nov. 24, 2006 in PCT Application No. PCT/US2005/046797.
"Apple Announces iTunes 2," Press Release, Apple Computer, Inc., Oct. 23, 2001.
"Apple Introduces iTunes—World's Best and Easiest to Use Jukebox Software," Macworld Expo, San Francisco, Jan. 9, 2001.
"Apple's iPod Available in Stores Tomorrow," Press Release, Apple Computer, Inc., Nov. 9, 2001.
"Nomad Jukebox," User Guide, Creative Technology Ltd., Version 1, Aug. 2000.
"SoundJam MP Plus Manual, version 2.0"—MP3 Player and Encoder for Macintosh by Jeffrey Robbin, Bill Kincaid and Dave Heller, manual by Tom Negrino, published by Casady & Greene, Inc., 2000.
"12.1" 925 Candela Mobile PC, downloaded from LCDHardware.com on Dec. 19, 2002, http://www.lcdharware.com/panel/12_1_panel/default.asp.
"BL82 Series Backlit Keyboards", www.tg3electronics.com/products/backlit/backlit.htm, downloaded Dec. 19, 2002.
"Bluetooth PC Headsets—Enjoy Wireless VoIP Conversations: 'Connecting' Your Bluetooth Headset With Your Computer", Bluetooth PC Headsets; downloaded on Apr. 29, 2006 from http://www.bluetoothpcheadsets.com/connect.htm.
"Creative MuVo TX 256 MB," T3 Magazine, Aug. 17, 2004, http://www.t3.co.uk/reviews/entertainment/mp3_player/creative_muvo_tx_256mb [downloaded Jun. 6, 2006].
"Digital Still Cameras—Downloading Images to a Computer," Mimi Chakarova et al., Multi-Media Reporting and Convergence, 2 pgs.
"Eluminx Illuminated Keyboard", downloaded Dec. 19, 2002, http://www.elumix.com/.
"How to Pair a Bluetooth Headset & Cell Phone", About.com; downloaded on Apr. 29, 2006 from http://mobileoffice.aboutcom/od/usingyourphone/ht/blueheadset_p.htm.
"Peripherals for Industrial Keyboards & Pointing Devices", Stealth Computer Corporation, downloaded on Dec. 19, 2002, http://www.stealthcomputer.com/peropherals_oem.htm.
"Poly-Optical Fiber Optic Membrane Switch Backlighting", downloaded Dec. 19, 2002, http://www.poly-optical.com/membrane_switches.html.
"Public Safety Technologies Tracer 2000 Computer", downloaded Dec. 19, 2002, http://www.pst911.com/traver.html.
"QuickTime Movie Playback Programming Guide", Apple Computer, Inc., Aug. 11, 2005.
"QuickTime Overview", Apple Computer, Inc., Aug. 11, 2005.
"Rocky Matrix Backlit Keyboard", downloaded Dec. 19, 2002, http://www.amrel.com/asi_matrixkeyboard.html.
"Sony Ericsson to introduce Auto pairing to improve Bluetooth connectivity between headsets and phones", Sep. 28, 2005 Press Release, Sony Ericsson Corporate; downloaded on Apr. 29, 2006 from http://www.sonyericsson.com/spg.jsp?cc=global&lc=en&ver=4001&template=pc3_1_1&z . . . .
"TAOS, Inc., Announces Industry's First Ambient Light Sensor to Convert Light Intensity to Digital Signals", www.taosinc.com/pressrelease_090902.htm, downloaded Jan. 23, 2003..
"Toughbook 28: Powerful, Rugged and Wireless", Panasonic: Toughbook Models, downloaded Dec. 19, 2002, http:www.panasonic.com/computer/notebook/html/01a_s8.htm.
"When it Comes to Selecting a Projection TV, Toshiba Makes Everything Perfectly Clear, Previews of New Releases", www.bestbuy.com/HomeAudioVideo/Specials/ToshibaTVFeatures.asp, downloaded. Jan. 23, 2003.
"WhyBuy: Think Pad", IBM ThinkPad Web Page Ease of Use, downloaded on Dec. 19, 2002, http://www.pc.ibm.com/us/thinkpad/easeofuse.html.
512MB Waterproof MP3 Player with FM Radio & Built-in Pedometer, Oregon Scientific, downloaded on Jul. 31, 2006 from http://www2.oregonscientific.com/shop/product.asp?cid=4&scid=11&pid=581.
Adam C. Engst, "SoundJam Keeps on Jammin'," Jun. 19, 2000, http://db.tidbits.com/getbits.acgi?tbart=05988.
Alex Veiga, "AT&T Wireless Launching Music Service," Yahoo! Finance, Oct. 5, 2004, pp. 1-2.
Andrew Birrell, "Personal Jukebox (PJB)," Oct. 13, 2000, http://birrell.org/andrew/talks/pjb-overview.ppt.
Apple iPod Technical Specifications, iPod 20GB and 60GB Mac + PC, downloaded from http://www.apple.com/ipod/color/specs.html on Aug. 8, 2005.
Bociurkiw, Michael, "Product Guide: Vanessa Matz,", www.forbes.com/asap/2000/1127/vmartz print.html, Nov. 27, 2000.

(56) References Cited

OTHER PUBLICATIONS

Compaq, "Personal Jukebox," Jan. 24, 2001, http://research.compaq.com/SRC/pjb/.
Creative: "Creative NOMAD MuVo TX," www.creative.com, Nov. 1, 2004, http://web.archive.org/web/20041024175952/www.creative.com/products/pfriendly.asp?product=9672 [downloaded Jun. 6, 2006].
Creative: "Creative NOMAD MuVo," www.creative.com, Nov. 1, 2004, http://web.archive.org/web/20041024075901/www.creative.com/products/product.asp?category=213&subcategory=215&product=110 [downloaded Jun. 7, 2006].
Creative: "MP3 Player," www.creative.com, Nov. 1, 2004, http://web.archive.org/web/20041024074823/www.creative.com/products/product.asp?category=213&subcategory=216&product=4983 [downloaded Jun. 7, 2006].
De Herrera, Chris, "Microsoft ActiveSync 3.1," Version 1.02, Oct. 13, 2000.
iAP Sports Lingo 0×09 Protocol V1.00, May 1, 2006.
IEEE 1394—Wikipedia, 1995, http://www.wikipedia.org/wiki/Firewire.
International Search Report dated Feb. 4, 2003 in corresponding application No. PCT/US2002/033330.
International Search Report dated Apr. 5, 2006 from corresponding International Application No. PCT/US2005/038819.
International Search Report dated Dec. 5, 2007 in PCT Application No. PCT/US2007/004810.
International Search Report dated Jul. 2, 2007 in related case PCT/US2006/048669.
International Search Report dated Jun. 19, 2007 in related Application PCT/US2006/048753.
International Search Report dated May 21, 2007 from corresponding PCT Application No. PCT/US2006/048670.
International Search Report in corresponding European Application No. 06256215.2 dated Feb. 20, 2007.
Invitation to Pay Additional Fees and Partial Search Report for corresponding PCT Application No. PCT/US2005/046797 dated Jul. 3, 2006.
iTunes 2, Playlist Related Help Screens, iTunes v2.0, Apple Computer, Inc., Oct. 23, 2001.
iTunes, Playlist Related Help Screens, iTunes v1.0, Apple Computer, Inc., Jan. 2001.
Jabra Bluetooth Headset User Manual; GN Netcom A/s, 2005.
Jabra Bluetooth Introduction; GN Netcom A/S, Oct. 2004.
Jabra FreeSpeak BT200 User Manual; Jabra Corporation, 2002.
Kennedy, "Digital Data Storage Using Video Disc," IBM Technical Disclosure Bulletin, vol. 24, No. 2, Jul. 1981.
Miniman, "Applian Software's Replay Radio and Player v1.02," Product review, pocketnow.com, http://www.pocketnow.com/reviews/replay/replay.htm, Jul. 31, 2001.
Musicmatch, "Musicmatch and Xing Technology Introduce Musicmatch Jukebox," May 18, 1998, http://www.musicmatch.com/info/company/press/releases/?year=1998&release=2.
Nonhoff-Arps, et al., "Straßenmusik Portable MP3-Spieler mit USB-Anschluss," CT Magazin Fuer Computer Technik, Verlag Heinz Heise GMBH, Hannover DE, No. 25, Dec. 4, 2000.
Partial Search Report dated Sep. 6, 2007 in PCT Application No. PCT/US2007/004810.
Personal Jukebox (PJB), "Systems Research Center and PAAD," Compaq Computer Corp., Oct. 13, 2000, http://research.compaq.com/SRC/pjb/.
Peter Lewis, "Two New Ways to Buy Your Bits," CNN Money, Dec. 31, 2003, pp. 1-4.
Sastry, Ravindra Wadali. "A Need for Speed: A New Speedometer for Runners", submitted to the Department of Electrical Engineering and Computer Science at the Massachusetts Institute of Technology, May 28, 1999.
Sinitsyn, Alexander. "A Synchronization Framework for Personal Mobile Servers," Pervasice Computing and Communications Workshops, 2004. Proceedings of the Second IEEE Annual Conference on, Piscataway, NJ, USA, IEEE, Mar. 14, 2004, pp. 208-212.
SoundJam MP Plus, Representative Screens, published by Casady & Greene, Inc., Salinas, CA, 2000.
Specification Sheet, iTunes 2, Apple Computer, Inc., Oct. 31, 2001.
Spiller, Karen. "Low-decibel earbuds keep noise at a reasonable level", The Telegraph Online, dated Aug. 13, 2006, http://www.nashuatelegraph.com/apps/pbcs.dll/article?Date=20060813&Cate . . . Downloaded Aug. 16, 2006.
Steinberg, "Sonicblue Rio Car," Product Review, Dec. 12, 2000, http://electronics.cnet.com/electronics/0-6342420-1304-4098389.html.
Travis Butler, "Archos Jukebox 6000 Challenges Nomad Jukebox," Aug. 13, 2001, http://db.tidbits.com/getbits.acgi?tbart=06521.
Travis Butler, "Portable MP3: The Nomad Jukebox," Jan. 8, 2001, http://db.tidbits.com/getbits.acgi?tbart=06261.
U.S. Appl. No. 11/621,541, "Personalized Podcasting Podmapping" filed Jan. 9, 2007.
Waterproof Music Player with FM Radio and Pedometer User Manual, Oregon Scientific, 2005.
Written Opinion dated Dec. 5, 2007 in PCT Application No. PCT/US2007/004810.
Partial Search Report and Invitation to Pay Fees dated Apr. 8, 2008 in PCT Application No. PCT/US2007/012033.
EP98928854.3 Supplementary Search Report Feb. 18, 2002.
PCT/US98/11268 International Search Report mailed Jan. 11, 1999.
PCT/US00/18237 International Search Report; Oct. 17, 2000.
PCT/US01/51620 International Search Report mailed Sep. 25, 2002.
PCT/US00/18237 International Preliminary Examination Report; Sep. 11, 2003.
Civil Action No. 05-CV-02323; Complaint, Nov. 16, 2005.
Civil Action No. 06-CV-01100-WDM-PAC, Complaint, Jun. 8, 2000.
Civil Action No. 06-CV-01100-WDM-PAC, Defendants Polar Electro Inc.'s and Polar Electro Oy's Answer and Affirmative Defenses: Polar Electro Inc.'s Counterclaim and Demand for Jury Trial, Jun. 29, 2006.
Civil Action No. 06-CV-01447-MSK-BNB, Complaint, Jul. 26, 2006.
Civil Action No. 06-CV-01447 MSK-BNB, First Amended Complaint; Aug. 16, 2006.
Civil Action No. 06-CV-01447-MSK-BNB, Answer, Affirmative Defenses, Counterclaim, and Demand for Jury Trial, Garmin; Sep. 26, 2006.
Civil Action No. 06-CV-01447-MSK-BNB; Garmin Disclosure Statement; Sep. 26, 2006.
Civil Action No. 06-CV-01447 MSK-BNB, Answer, Affirmative Defenses, Counterclaims and Demand for Jury Trial, Timex; Sep. 26, 2006.
Civil Action No. 06-CV-01447-MSK-BNB; Timex Disclosure Statement; Sep. 26, 2006.
Civil Action No. 06-CV-01447-MSK-BNB: PhatRat Technology, Inc.'s Supplemental Answers and Objections to Defendant, Timex Corporation's Interrogatories Nos. 1, 2, 5, 7-11, 13 and 15; Feb. 12, 2007.
Civil Action No. 06-CV-02122-REB-MJW, Complaint, Oct. 24, 2006.
Civil Action No. 06-CV-02122-REB-MJW, Apple Computer, Inc.'s Answer to Complaint and Counterclaims, Jan. 22, 2007.
Civil Action No. 07-CV-00078-MSK-BNB, Complaint, Jan. 12, 2007.
Civil Action No. 07-CV-00078-MSK-BNB, Answer, Feb. 9, 2007.
Civil Action No. 07-CV-00238-REB-PAC Complaint, Mar. 19, 2007.
Civil Action No. 07-CV-00238-REB, Apple Inc.'s Answer to Complaint, Counterclaims and Jury Demand, Mar. 19, 2007.
Civil Action No. 07-CV-00238; Nike Inc.'s Answer, Affirmative Defenses to First Complaint, Mar. 19, 2007.
U.S. Appl. No. 08/764,758, Office Action mailed Aug. 21, 1997.
U.S. Appl. No. 08/764,758, Response to Office Action mailed Aug. 21, 1997.
U.S. Appl. No. 08/764,758, Office Action mailed Dec. 15, 1998.
U.S. Appl. No. 08/764,758, Response to Office Action mailed Dec. 15, 1998.
U.S. Appl. No. 08/764,758, Office Action mailed May 8, 1998.

(56) References Cited

OTHER PUBLICATIONS

U.S. Appl. No. 08/764,758, Response to Office Action mailed May 8, 1998, filed Oct. 8, 1998.
U.S. Appl. No. 08/764,758, Notice of Allowance mailed Jun. 1, 1999.
U.S. Appl. No. 08/764,758, Advisory Action mailed Apr. 29, 1999.
U.S. Appl. No. 08/867,083, Office Action mailed Apr. 8, 1999.
U.S. Appl. No. 08/764,758, Rule 116 Amendment filed Apr. 8, 1999.
U.S. Appl. No. 08/764,758, Rule 116 Amendment filed May 13, 1999.
U.S. Appl. No. 08/867,083, Response to Office Action mailed Apr. 8, 1999.
U.S. Appl. No. 08/867,083, Supp. Response to Office Action mailed Apr. 8, 1999.
U.S. Appl. No. 08/867,083, Final Office Action mailed Jan. 3, 2000.
U.S. Appl. No. 08/867,083, Notice of Appeal mailed Jan. 3, 2000.
U.S. Appl. No. 08/867,083, Notice of Appeal Response to Office Action mailed Jan. 3, 2000.
U.S. Appl. No. 08/867,083, Advisory Action mailed Mar. 14, 2000.
U.S. Appl. No. 08/867,083 Office Action mailed Jun. 26, 2000.
U.S. Appl. No. 08/867,083 Amendment response to Office Action mailed Jun. 26, 2000.
U.S. Appl. No. 08/867,083 Notice of Allowance, mailed Feb. 6, 2001.
U.S. Appl. No. 09/089,232, Information Disclosure Statement mailed Oct. 23, 1998.
U.S. Appl. No. 09/089,232, Office Action mailed Nov. 27, 1998.
U.S. Appl. No. 09/089,232, Office Action mailed May 30, 2000.
U.S. Appl. No. 09/089,232, Preliminary Amendment response to Office Action mailed May 30, 2000.
U.S. Appl. No. 09/089,232, Office Action mailed Dec. 19, 2000.
U.S. Appl. No. 09/089,232, Response to Office Action mailed Dec. 19, 2000.
U.S. Appl. No. 09/089,232, Office Action mailed Aug. 8, 2001.
U.S. Appl. No. 09/089,232, Notice of Appeal mailed Nov. 5, 2001.
U.S. Appl. No. 09/089,232, Notice of Appeal mailed Nov. 7, 2001.
U.S. Appl. No. 09/089,232, Appeal Brief mailed Jan. 2, 2002.
U.S. Appl. No. 09/089,232, Office Action mailed Apr. 26, 2002.
U.S. Appl. No. 09/089,232, Appeal Brief mailed Jul. 26, 2002.
U.S. Appl. No. 09/089,232, Notice of Allowance mailed Oct. 2, 2002.
U.S. Appl. No. 09/089,232, Comments on Allowance mailed Oct. 16, 2002.
U.S. Appl. No. 09/089,232, Office Action mailed Jan. 27, 2003.
U.S. Appl. No. 09/698,659, Office Action mailed Mar. 19, 2002.
U.S. Appl. No. 09/698,659, Response to Office Action of Mar. 19, 2002.
U.S. Appl. No. 09/698,659, Office Action mailed Nov. 21, 2002.
U.S. Appl. No. 09/698,659, Response to Office Action of Nov. 21, 2002.
U.S. Appl. No. 09/698,659, Notice of Allowance mailed Apr. 9, 2003.
U.S. Appl. No. 09/848,445, Preliminary Amendment mailed Dec. 5, 2001.
U.S. Appl. No. 09/848,445, Office Action mailed Dec. 5, 2003.
U.S. Appl. No. 09/848,445, Response to Office Action mailed Dec. 5, 2003.
U.S. Appl. No. 09/848,445, Office Action mailed May 6, 2004.
U.S. Appl. No. 09/848,445, Response to Office Action (Rule 116) mailed May 6, 2004.
U.S. Appl. No. 09/886,578, Preliminary Amendment mailed Jun. 21, 2001.
U.S. Appl. No. 09/886,578, Office Action mailed Nov. 8, 2001.
U.S. Appl. No. 09/886,578, Response to Office Action mailed Nov. 8, 2001.
U.S. Appl. No. 09/886,578, Office Action mailed Jun. 5, 2002.
U.S. Appl. No. 09/886,578, Response to Office Action mailed Jun. 5, 2002.
U.S. Appl. No. 09/886,578, Notice of Allowance mailed Sep. 9, 2002.
U.S. Appl. No. 09/992,966, Office Action mailed Feb. 3, 2003.
U.S. Appl. No. 09/992,966, Response to Office Action mailed Feb. 3, 2003.
U.S. Appl. No. 09/992,966, Office Action mailed Mar. 28, 2002.
U.S. Appl. No. 09/992,966, Response to Office Action mailed Mar. 28, 2002.
U.S. Appl. No. 09/992,966, Office Action mailed Jul. 18, 2003.
U.S. Appl. No. 09/992,966, Response to Office Action mailed Jul. 18, 2003.
U.S. Appl. No. 09/992,966, Examiner Summary mailed Oct. 27, 2003.
U.S. Appl. No. 09/992,966, Notice of Allowance mailed Apr. 15, 2004.
U.S. Appl. No. 09/992,966, Office Action mailed Jan. 6, 2004.
U.S. Appl. No. 09/992,966, Response to Office Action mailed Jan. 6, 2004.
U.S. Appl. No. 09/992,966, Notice of Allowance mailed Sep. 3, 2004.
U.S. Appl. No. 10/234,660, Office Action mailed Mar. 31, 2003.
U.S. Appl. No. 10/234,660, Response to Office Action mailed Mar. 31, 2003.
U.S. Appl. No. 10/234,660, Final Office Action mailed Oct. 31, 2003.
U.S. Appl. No. 10/234,660, Dec. 23, 2003 Response to Office Action mailed Oct. 31, 2003.
U.S. Appl. No. 10/234,660 Response and Amendment Under 37 CFR Section 1.116 mailed Oct. 31, 2003.
U.S. Appl. No. 10/234,660; Advisory Action mailed Jan. 27, 2004.
U.S. Appl. No. 10/234,660; Appeal Brief filed Jun. 14, 2004.
U.S. Appl. No. 10/234,660; Amendment filed Jul. 20, 2004.
U.S. Appl. No. 10/234,660; Marked up Claims by USPTO dated Jul. 28, 2004.
U.S. Appl. No. 10/234,660; Notice of Allowance; Aug. 2, 2004.
U.S. Appl. No. 10/297,270 Office Action mailed Jul. 29, 2004.
U.S. Appl. No. 10/297,270 Response to Office Action mailed Jul. 29, 2004.
U.S. Appl. No. 10/297,270 Office Action mailed Dec. 13, 2004.
U.S. Appl. No. 10/297,270 Response to Office Action mailed Dec. 13, 2004.
U.S. Appl. No. 10/297,270 Request Deletion of Named Inventors Pursuant to 37 CFR § 1.63 (d)(2) received by the Patent Office on Oct. 4, 2002.
U.S. Appl. No. 10/297,270 Office Action mailed Jul. 13, 2005.
U.S. Appl. No. 10/297,270 Response to Office Action mailed Jul. 13, 2005.
U.S. Appl. No. 10/297,270 Office Action mailed Feb. 9, 2006.
U.S. Appl. No. 10/297,270 Response to Office Action mailed Feb. 9, 2006.
U.S. Appl. No. 10/297,270 Office Action mailed Sep. 25, 2006.
U.S. Appl. No. 10/297,270 Response to Office Action mailed Sep. 25, 2006.
U.S. Appl. No. 10/297,270 Office Action mailed Jan. 11, 2007.
U.S. Appl. No. 10/297,270 Response to Office Action mailed Jan. 11, 2007.
U.S. Appl. No. 10/297,270 Office Action mailed Jul. 26, 2007.
U.S. Appl. No. 10/297,270 Response to Office Action mailed Jul. 26, 2007.
U.S. Appl. No. 10/601,208 Preliminary Amendment, mailed Jun. 20, 2003.
U.S. Appl. No. 10/601,208 Office Action mailed Jun. 15, 2004.
U.S. Appl. No. 10/601,208 Response to Office Action mailed Jun. 15, 2004.
U.S. Appl. No. 10/601,208 Office Action mailed Aug. 26, 2004.
U.S. Appl. No. 10/601,208 Response to Office Action mailed Aug. 26, 2004.
U.S. Appl. No. 10/601,208 Second Response to Office Action mailed Aug. 26, 2004.
U.S. Appl. No. 10/601,208 Office Action mailed May 11, 2005.
U.S. Appl. No. 10/601,208 Response to Office Action mailed May 11, 2005.
U.S. Appl. No. 10/601,208 Office Action mailed Feb. 15, 2006.
U.S. Appl. No. 10/601,208 Response to Office Action mailed Feb. 15, 2006.
U.S. Appl. No. 10/601,208 Office Action mailed Sep. 26, 2006.
U.S. Appl. No. 10/601,208 Response to Office Action mailed Sep. 26, 2006.
U.S. Appl. No. 10/601,208 Notice of Allowance mailed Dec. 8, 2006.
U.S. Appl. No. 10/842,947, Preliminary Amendment mailed May 11, 2004.

(56) References Cited

OTHER PUBLICATIONS

U.S. Appl. No. 10/842,947, Office Action mailed Nov. 30, 2004.
U.S. Appl. No. 10/842,947, Response to Office Action mailed Nov. 30, 2004.
U.S. Appl. No. 10/842,947, Office Action mailed Jun. 30, 2005.
U.S. Appl. No. 10/842,947, Response to Office Action mailed Jun. 30, 2005.
U.S. Appl. No. 10/842,947, Notice of Allowance mailed Feb. 9, 2006.
U.S. Appl. No. 10/921,743; Office Action mailed Mar. 4, 2005.
U.S. Appl. No. 10/921,743; Response to Office Action mailed Mar. 4, 2005.
U.S. Appl. No. 10/921,743; Office Action mailed May 26, 2005.
U.S. Appl. No. 10/921,743; Response to Office Action mailed May 26, 2005.
U.S. Appl. No. 10/921,743; Office Action mailed Sep. 13, 2005.
U.S. Appl. No. 10/921,743; Advisory mailed Nov. 25, 2005.
U.S. Appl. No. 10/921,743; Response to Office Action mailed Sep. 13, 2005 and Advisory mailed Nov. 25, 2005.
U.S. Appl. No. 10/921,743; Notice of Allowance; Feb. 16, 2006.
U.S. Appl. No. 10/950,897, Office Action mailed Mar. 7, 2005.
U.S. Appl. No. 10/950,897, Response to Office Action mailed Mar. 7, 2005.
U.S. Appl. No. 10/950,897, Office Action mailed Jun. 23, 2005.
U.S. Appl. No. 10/950,897, Response to Office Action mailed Jun. 23, 2005.
U.S. Appl. No. 10/950,897, Office Action mailed Sep. 9, 2005.
U.S. Appl. No. 10/950,897, Response to Office Action mailed Sep. 9, 2005.
U.S. Appl. No. 10/950,897, Office Action mailed Nov. 25, 2005.
U.S. Appl. No. 10/950,897, Response to Office Action mailed Nov. 25, 2005.
U.S. Appl. No. 10/950,897, Amendment to Notice of Allowance mailed Dec. 13, 2005.
U.S. Appl. No. 11/221,029; Preliminary Amendment dated Aug. 22, 2006.
U.S. Appl. No. 11/221,029; Office Action mailed Sep. 8, 2006.
U.S. Appl. No. 11/221,029; Response to Office Action mailed Sep. 8, 2006.
U.S. Appl. No. 11/221,029; Notice of Allowance; Oct. 3, 2006.
U.S. Appl. No. 11/252,576; Notice of Allowance; Dec. 11, 2007.
U.S. Appl. No. 11/358,508; Notice of Non Compliance mailed Sep. 12, 2006.
U.S. Appl. No. 11/358,508, Preliminary Amendment mailed Mar. 30, 2006.
U.S. Appl. No. 11/358,508, Preliminary Amendment mailed May 30, 2006.
U.S. Appl. No. 11/358,508, Preliminary Amendment mailed Jul. 26, 2006.
U.S. Appl. No. 11/358,508, Office Action mailed Aug. 14, 2006.
U.S. Appl. No. 11/358,508, Response to Office Action mailed Aug. 14, 2006.
U.S. Appl. No. 11/358,508, Response to Notice mailed Sep. 12, 2006.
U.S. Appl. No. 11/358,508, Notice of Allowability & Interview Summary mailed Oct. 18, 2006.
U.S. Appl. No. 11/358,508, Rule 312 Amendment mailed Oct. 24, 2006.
U.S. Appl. No. 11/434,588: Office Action mailed Jan. 31, 2007.
U.S. Appl. No. 11/434,588; Response to Office Action mailed Jan. 31, 2007.
U.S. Appl. No. 11/434,588; Notice of Allowance; Jul. 11, 2007.
U.S. Appl. No. 11/434,588; Notice of Allowance; Nov. 6, 2007.
U.S. Appl. No. 11/484,199 Preliminary Amendment; Sep. 7, 2006.
U.S. Appl. No. 11/484,199 Notice of Allowance and Examiner Interview Summary; Oct. 6, 2006.
U.S. Appl. No. 11/598,410, Office Action mailed Jun. 13, 2007.
U.S. Appl. No. 11/598,410 Response to Office Action mailed Jun. 13, 2007.
U.S. Appl. No. 11/598,410, Notice of Allowability Sep. 26, 2007.
U.S. Appl. No. 11/646,768, Office Action mailed May 7, 2007.
U.S. Appl. No. 11/646,768, Response to Office Action mailed May 7, 2007.
U.S. Appl. No. 11/646,768, Office Action mailed Oct. 29, 2007.
U.S. Appl. No. 11/646,768, Response to Office Action mailed Oct. 29, 2007.
U.S. Appl. No. 11/646,768; Notice of Allowance; Jan. 18, 2008.
U.S. Appl. No. 11/747,081; Office Action mailed Jan. 24, 2008.
Cole, George, "The Little Label with an Explosion of Applications", Financial Times, Ltd., 2002, pp. 1-3.
Deem, "Fast Forward Go for a Ride on the World's Fastest Sailboat", Popular Mechanics, www.popularmechanics.com, Feb. 2001, pp. 1-2.
Desmarais, "Solutions in Hand", BEI Technologies, Inc., www.sensormag.com, Jan. 2001, pp. 1-2.
Desmarais et al., "How to select and use the right temperature," www.sensorsmag.com, Jan. 2001, pp. 30-36.
GPS Locator for Children, Klass Kids Foundation Jul. 15, 2004.
Henkel, Research & Developments, *Sensors*, Nov. 2000. p. 18.
Janssens et al., "Columbus: A Novel Sensor System for Domestic Washing Machines", *Sensors Magazine* Online, Jun. 2002, pp. 1-9.
Licking, Special Report: E-Health, "This is the Future of Medicine", Business Week E.Biz, Dec. 11, 2000, pp. 77 and 78 US.
Li-Ron, Tomorrow's Cures, Health & Fitness Special Section Online, Newsweek, Dec. 10, 2001, pp. 3-10.
Mark of Fitness Flyer, "High Quality, Self-Taking Blood Pressure Monitors", four pages, Shrewsbury, NJ, US.
Martella, Product News, "Temperature Monitoring System", Nov. 2000, p. 77.
Nobbe, "Olympic Athletes Get a Boost from Technology", *Machine Design*, vol. 60, No. 19, Aug. 25, 1988.
Paradiso et al., Design and Implementation of Expressive Footwear, May 12, 2000, IBM Systems Journal, vol. 39, Nos. 3 & 4, pp. 511-529.
Paradiso, et al. "Instrumented Footwear for Interactive Dance" Version 1.1, Presented at the XII Colloquium on Musical Informatics, Gorizia, Italy, Sep. 24-26, 1998, pp. 1-4.
Sellers. Gear to Go, Mitch Mandel Photography, Mar. 2001, pp. 61-62.
Shannon P. Jackson and Harold Kirkham, "Weighing Scales Based on Low-Power Strain-Gauge Circuits", NASA Tech Briefs, Jun. 2001, p. 49 US.
Sharp, A Sense of the Real World, www.idsystems.com/reader/2000_09/sens0900.htm, Sep. 2000, 4 pages.
Skaloud et al., DGPS-Calibrated Accelerometric System for Dynamic Sports Events, Sep. 19-22, 2000, ION GPS 2000.
Smith et al., "Flexible and Survivable Non-Volatile Memory Data Recorder", AFRL Technology Horizons, Dec. 2000, p. 26.
Webster's II New Riverside University Dictionary, 1988, The Riverside Publishing Company, p. 1138.
Wysocki, Jr., Staff Reporter, "Do Devices Measuring Body Signs Appeal to the Sick or Healthy", Pittsburgh, US.
No author listed, "Ever Forget to Bring Your Cell Phone or Keys?", Catalog Page, PI Manufacturing Corp, 20732 Currier Rd., Walnut, CA 91789, Home Office Accessory, Catalog Nos. TA-100N; TA-100M; TA-100F, US.
No author listed, "Your Next . . . ", *Newsweek*, Jun. 25, 2001, p. 52 US.
No author listed, The GPS Connection, *Popular Mechanics*, Feb. 2001, p. 65.
No author listed, WarmMark Time Temperature Indicators, www.coldice.com/warmmark_temperature_indicators.html, Cold Ice., Inc.
No author listed, Wireless Temperature Monitor, www.echo-on.net/mob/, Nov. 20, 2000.
Unattributed, 3M MonitorMark Indicator Data Sheet [online], [retrieved on Aug. 9, 2004], retrieved from the Internet: URL: http://www.3m.corn/us/healthcare/medicalspecialties/monitor/products.html; 4 pages.
International Search Report dated Jul. 7, 2008 in PCT Application No. PCT/US2007/012033.
Written Opinion dated Jul. 7, 2008 in PCT Application No. PCT/US2007/012033.
Office Action dated Oct. 29, 2008 in U.S. Appl. No. 11/566,072.
Office Action dated Apr. 14, 2009 in U.S. Appl. No. 11/439,523.

(56) References Cited

OTHER PUBLICATIONS

Office Action dated Mar. 4, 2009 in U.S. Appl. No. 11/513,616.
Office Action dated Apr. 2, 2009 in U.S. Appl. No. 11/683,391.
Notice of Allowance dated Oct. 8, 2009 in U.S. Appl. No. 11/439,523.
Office Action dated Aug. 20, 2009 in U.S. Appl. No. 11/513,616.
Office Action dated Sep. 17, 2009 in U.S. Appl. No. 11/683,391.
Office Action dated Aug. 5, 2010 in Australian Application No. 2007268089.
Office Action dated Aug. 24, 2010 in EP Application No. 07 795 093.9.
Office Action dated Sep. 30, 2010 in U.S. Appl. No. 11/419,737.
Office Action dated Feb. 25, 2010 in Australian Application No. 2007268089.
Office action dated Mar. 15, 2010 in U.S. Appl. No. 11/513,692.
Notice of Allowance dated Dec. 31, 2009 in U.S. Appl. No. 11/683,391.
Office Action dated Dec. 2, 2009 in U.S. Appl. No. 11/513,616.
Notice of Allowance dated Aug. 9, 2011 from U.S. Appl. No. 12/713,103.
U.S. Office Action dated Dec. 27, 2010 from U.S. Appl. No. 12/713,103.
U.S. Office Action dated Jul. 20, 2011 from U.S. Appl. No. 11/419,737.
U.S. Office Action dated Mar. 7, 2011 from U.S. Appl. No. 11/419,737.
U.S. Office Action dated May 27, 2011 from U.S. Appl. No. 12/713,103.

* cited by examiner

CALIBRATION TECHNIQUES FOR ACTIVITY SENSING DEVICES

CROSS-REFERENCE TO RELATED APPLICATIONS

This application claims the priority benefit of U.S. Provisional Patent Application No. 60/802,889, filed May 22, 2006, and entitled "ACTIVITY MONITORING SYSTEM", which is hereby incorporated by reference herein.

This application is also related to: (i) U.S. patent application Ser. No. 11/566,072, filed Dec. 1, 2006, and entitled "ACTIVITY MONITORING SYSTEM"; (ii) U.S. patent application Ser. No. 11/439,521, filed May 22, 2006, and entitled "COMMUNICATION PROTOCOL FOR USE WITH PORTABLE ELECTRONIC DEVICES," which is hereby incorporated by reference herein; (iii) U.S. patent application Ser. No. 11/419,737, filed May 22, 2006, and entitled "INTEGRATED MEDIA JUKEBOX AND PHYSIOLOGIC DATA HANDLING APPLICATION," which is hereby incorporated by reference herein; and (iv) U.S. patent application Ser. No. 11/439,523, filed May 22, 2006, and entitled "PORTABLE MEDIA DEVICE WITH WORKOUT SUPPORT," which is hereby incorporated by reference herein.

BACKGROUND OF THE INVENTION

1. Field of the Invention

The present invention relates to activity monitoring and, more particularly, to activity monitoring by portable electronic devices.

2. Description of the Related Art

A media player stores media assets, such as audio tracks, that can be played or displayed on the media player. One example of a portable media player is the iPod® media player, which is available from Apple Computer, Inc. of Cupertino, Calif. Often, a media player acquires its media assets from a host computer that serves to enable a user to manage media assets. In managing media assets, a user can create playlists for audio tracks. These playlists can be created at the host computer. Media assets within the playlists can then be copied to the media player. As an example, the host computer can execute a media management application to acquire and manage media assets. One example of a media management application is iTunes® produced by Apple Computer, Inc.

Portable media players, such as MP3 players, are able to play music for users often via earphones or a headset. Typically, portable media players are dedicated to playing media. Lately, media players have been integrated into mobile telephones as well as personal information managers (or digital personal assistants). However, many users of portable media players utilize their media players in the context of exercising, such as at the gym or while running outdoors. Unfortunately, however, portable media players are not designed to assist the users in the context of their exercising. Although portable media players can play music for the users, there is traditionally no capability to provide any non-media information to the user.

One existing approach is to use a wristwatch including GPS technology to track distance of runs, but such lacks the ability to provide media playback. While GPS may not require a calibration operation, GPS technology itself is unable to provide high precision monitoring and is dependent on being able to interact in a wireless manner with satellites.

Another existing approach is a speedometer system that includes a watch worn on a user's wrist and a small foot worn device on the user's shoe. The speedometer system can provide the user with information concerning speed, pace, distance and calories while running or walking. The speedometer system requires that the user perform one or more calibration operations to enhance accuracy. The calibration operation requires that the user run on a track or treadmill for an accurate distance. Such calibration operations are not only burdensome on its users but also can often lack accuracy.

Recently, a MP3 player has been enhanced to support wireless communications, through a Bluetooth module, with a wireless speed and distance sensor that is coupled to the shoelaces of the user's shoe. The wireless speed and distance sensor operates as a pedometer and can wirelessly transmit data to the MP3 player. Such a system permits interaction between a MP3 player and a pedometer, which are conventionally separate devices. This system also requires that the user perform one or more calibration operations to enhance accuracy. Such calibration operations are not only burdensome on its users but also can often lack accuracy.

Regardless, there remains a need for improved accuracy of sensing systems for use in or with portable media players or other electronic devices so that users are able to monitor their exercise.

SUMMARY OF THE INVENTION

The invention relates to improved techniques and systems to calibrate an electronic device that is providing activity sensing. The activity being sensed can, for example, correspond to walking or running by a user. In one embodiment, calibration can be performed by a portable electronic device so that activity data it receives from a remote sensor device can be more accurately processed.

The improved techniques to calibrate can be used by a portable electronic device to monitor, process, present and manage data captured by a remote sensor. The portable electronic device can also offer a convenient user interface that can be visual and/or audio based, customized to a particular application, user-friendly and/or dynamic. The portable electronic device can pertain to a portable media player and thus also provide media playback.

The invention can be implemented in numerous ways, including as a method, system, device, apparatus (including graphical user interface), or computer readable medium. Several embodiments of the invention are discussed below.

As a method for calibrating an activity monitoring system associated with a user, one embodiment of the invention includes at least the acts of: providing the activity monitoring system with default calibration data; performing a first calibration to produce first modified calibration data, the first modified calibration data being derived from the default calibration data; and subsequently performing a second calibration to produce second modified calibration data, the second modified calibration data being derived from the first modified calibration data.

As a method for calibrating an activity monitoring system associated with a user, one embodiment of the invention includes at least the acts of: receiving a calibration request from the user; receiving an indication of a calibration distance; awaiting a calibration start indication before starting activity to be used for calibration; receiving activity data from an activity sensor associated with the activity monitoring system during the activity for calibration; estimating at least one of pace and distance based on the received activity data and an existing calibration model; awaiting receipt of a calibration stop indication; repeating the receiving and the estimating until the calibration stop indication is received; and modifying the existing calibration model based on at least the estimated distance from the estimating and the calibration distance.

As a method for operating an activity monitoring apparatus associated with a user utilizing at least one shoe, one embodiment of the invention includes at least the acts of: receiving shoe characteristic information pertaining to the shoe; and operating the activity monitoring apparatus based at least in part on the shoe characteristic information.

As a portable electronic device, one embodiment of the invention includes at least: a user interface for providing user input to the portable electronic device and user output from the portable electronic device; a calibration model; an activity application that operates to monitor a physiological characteristic of a user of the portable electronic device, the activity application receives sensor data acquired from a remote sensor associated with the user, and the activity application processes the sensor data in view of the calibration model; a calibration engine that operates to modify the calibration model in view of a calibration activity for which sensor data from the remote sensor is acquired and processed by the activity application or the calibration engine.

As a computer readable medium including at least computer program code for calibrating an activity monitoring system associated with a user, one embodiment of the invention includes at least: computer program code for performing a first calibration to produce first modified calibration data, the first modified calibration data being derived from existing calibration data; and computer program code for subsequently performing a second calibration to produce second modified calibration data, the second modified calibration data being derived from the first modified calibration data.

As a computer readable medium including at least computer program code for calibrating an activity monitoring system associated with a user, another embodiment of the invention includes at least: computer program code for receiving an indication of a calibration distance; computer program code for awaiting a start indication before starting activity to be used for calibration; computer program code for receiving activity data from an activity sensor associated with the activity monitoring system during the activity to be used for calibration; computer program code for estimating at least one of pace and distance based on the received activity data and an existing calibration model; computer program code for awaiting receipt of a stop indication that indicates the end of the activity to be used for calibration; and computer program code for modifying the existing calibration model based on at least the estimated distance and the calibration distance.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which.

DETAILED DESCRIPTION OF THE INVENTION

One aspect of the invention pertains to improved techniques to calibrate an electronic device that is providing activity sensing. The activity being sensed can, for example, correspond to walking or running by a user. In one embodiment, calibration can be performed by a portable electronic device so that activity data it receives from a remote sensor device can be more accurately processed.

The improved techniques to calibrate can be used by a portable electronic device to monitor, process, present and manage data captured by a remote sensor. The portable electronic device can also offer a convenient user interface that can be visual and/or audio based, customized to a particular application, user-friendly and/or dynamic. The portable electronic device can pertain to a portable media player and thus also provide media playback.

The invention is particularly well suited for use in monitoring sports-related data, such as exercise data (e.g., run data). However, it should be recognized that the invention is not limited to sports monitoring, but instead is applicable to any type of monitoring. For example, the monitoring can be any physiological monitoring of a person, who is typically the user of a portable electronic device.

Embodiments of the invention are discussed below with reference to FIGS. 1-20. However, those skilled in the art will readily appreciate that the detailed description given herein with respect to these figures is for explanatory purposes as the invention extends beyond these limited embodiments.

Figure 1:
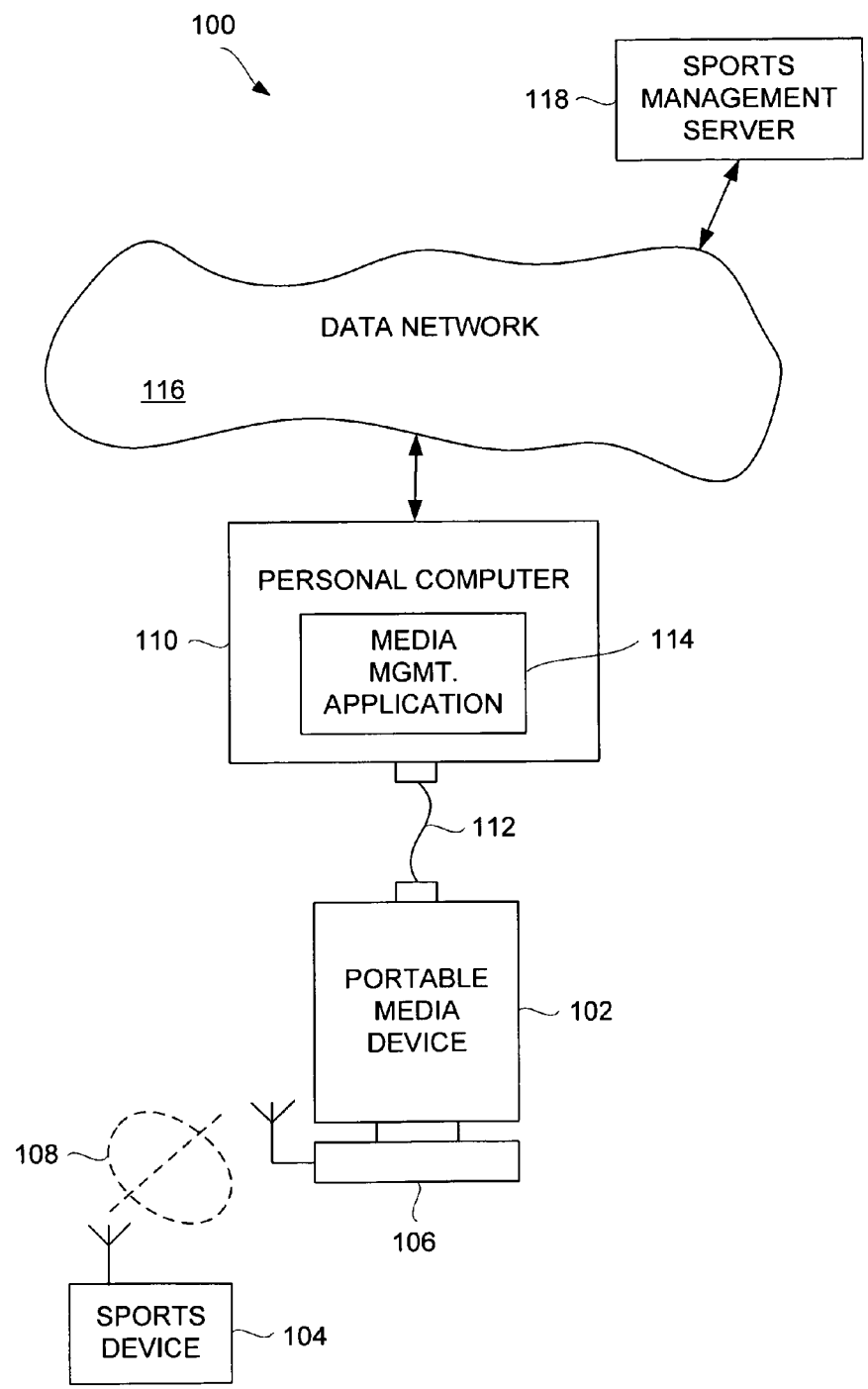
FIG. 1 is a block diagram of a sports monitoring system according to one embodiment of the invention.

FIG. 1 is a block diagram of a sports monitoring system 100 according to one embodiment of the invention. The sports monitoring system 100 is an electronic system that enables sports related information to be acquired, stored, analyzed, presented and shared.

The sports monitoring system 100 includes a portable media device 102. The portable media device 102 is capable of storing and playing media for its user. For example, the portable media device 102 can output (e.g., play) audio or video. The sports monitoring system 100 also includes a sports device 104. The sports device 104 is, for example, a pedometer, a heart rate monitor, etc. The sports device 104 includes one or more sensors that acquire sports related data.

The sports device 104 also includes wireless transmission capability so that the sports related data can be transmitted to the portable media device 102. In particular, the portable media device 102 includes a wireless interface accessory 106. The wireless interface accessory 106 includes a wireless transceiver so that the wireless interface accessory 106 can receive the sports related data being transmitted by the sports device 104 by way of a wireless connection through a personal wireless network 108. The portable media device 102 can receive the sports related data from the sports device 104 via the wireless interface accessory 106 and can then operate to process and store the sports related data at the portable media device 102.

The sports monitoring system 100 also includes a personal computer 110. The portable media device 102 can be electrically connected to the personal computer 110 by way of a cable 112. The cable 112 can, for example, be a Firewire or USB cable. Alternatively, the cable 112 can be replaced with a wireless link. Although the portable media device 102 is not normally electrically connected to the personal computer 110, the electrical connection, when present, facilitates information exchange between the portable media device 102 and the personal computer 110.

The personal computer 110 includes a media management application 114. The media management application 114, in one embodiment, can not only manage the media assets stored on the personal computer 110, but can also store and manage sports related data. In one embodiment, the media management application 114 can operate to cause the sports related data stored on the portable media device 102 to be copied to the personal computer 110. Thereafter, the sports related data can be analyzed at the personal computer 110 and/or made available to the user of the personal computer 110. In addition, the sports monitoring system 100 can facilitate the personal computer 110 coupling to a data network 116. The data network 116 can represent a global or wide area network, such as the World Wide Web (or the Internet). When the personal computer 110 is coupled to the data network 116, the sports related data present at the personal computer 110 can be transferred to a sports management server 118. At the sports management server 118, the sports related data can be further analyzed and/or processed to facilitate usefulness of the data. The sports management server 118 supports storage and analysis of sports related data from a large number of different portable media devices and/or personal computers. Hence, the sports management server 118 can also compare the sports related data from different users. The sports management server 118 can also provide a website that can be accessed by a network browser operating on the personal computer 110 or other computing device to access sports related information or other information made available via the website.

The sports monitoring system 100 can also support one or more remote controllers (not shown). A remote controller can also communicate with a portable media device 102 via the wireless interface accessory 106. The remote controller may require it be paired or linked with the wireless interface accessory 106 or the portable media device 102.

The sports device 104 illustrated in FIG. 1 can take a variety of different forms. In one embodiment, the sports device is a sensor-based device. One example of a sensor-based device is a pedometer.

Although the sports monitoring system 100 illustrated in FIG. 1 provides the wireless interface accessory 106 apart from the media device 102, in another embodiment, the functionality (e.g., wireless interface) provided by the wireless interface accessory 106 can be provided by the media device 102 itself.

Figure 2:
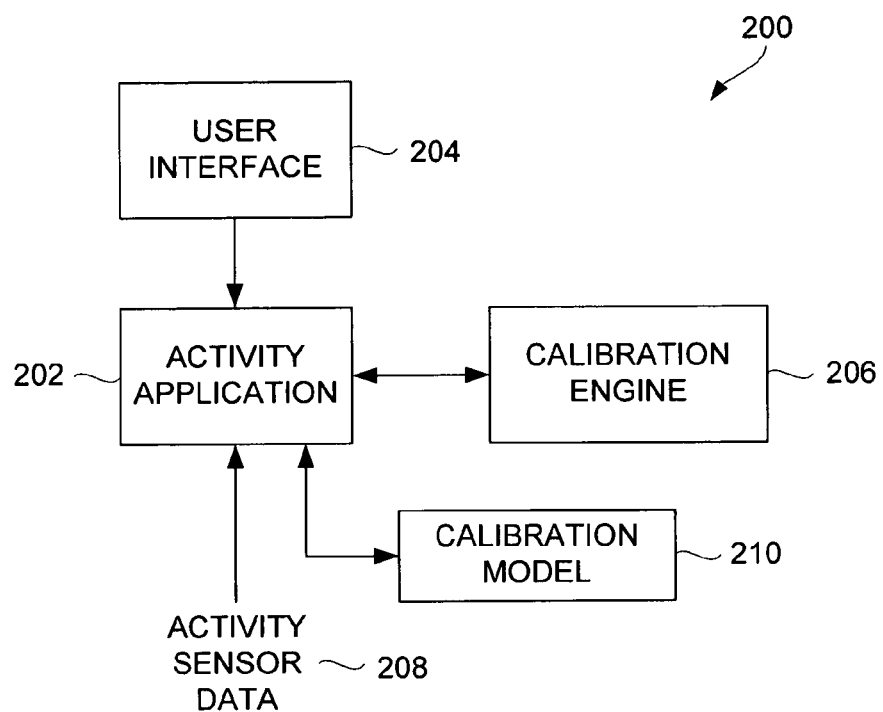
FIG. 2 is an activity monitoring system for an electronic device according to one embodiment of the invention.

FIG. 2 is an activity monitoring system 200 for an electronic device according to one embodiment of the invention. The electronic device is, for example, a portable media device, such as the portable media device 102 illustrated in FIG. 1. The activity monitoring system 200 includes an activity application 202. The activity application 202 is a software program that operates on the electronic device. In one example, the activity application 202 can facilitate and manage workout monitoring of workouts that are performed by a user of the electronic device.

The activity monitoring system 200 also includes a user interface 204. The user interface 204 can be utilized to provide user inputs that can be used by the activity application 202. For example, one particular user input is a request for calibration. FIGS. 7-15, which are discussed below, illustrate exemplary screens of a graphical user interface that can enable a user to request calibration. When the activity application 202 receives a request for calibration, the activity application 202 starts a calibration process that is performed by the activity application 202 together with a calibration engine 206. The calibration process makes use of activity sensor data 208 that is supplied to the electronic device from an activity sensor. The activity sensor is typically separate from the electronic device. The activity sensor transmits activity sensor data 208 to the electrical device. At the electrical device, the activity application 202 can receive the activity sensor data 208.

The activity application 202 can process the activity sensor data in conjunction with a calibration model 210. The calibration model 210 is a stored calibration model for use by the electronic device. In one embodiment, the calibration model 210 is customized to the user of the electronic device. In addition, the activity application 202 provides processed activity data as well as the calibration model 210 to the calibration engine 206. The calibration engine 206 can then determine, typically at the end of the calibration process, whether and how to modify the calibration model 210 so that the activity application 202 is able to more accurately interpret the activity sensor data 208. In other words, the calibration engine 206 operates to cause the calibration model 210 to be modified so as to better fit the characteristics of the user of the electronic device. Either the calibration engine 206 or the activity application 202 can change the calibration model 210. Thereafter, the activity application 202 is able to provide more accurate activity monitoring.

Figure 3:
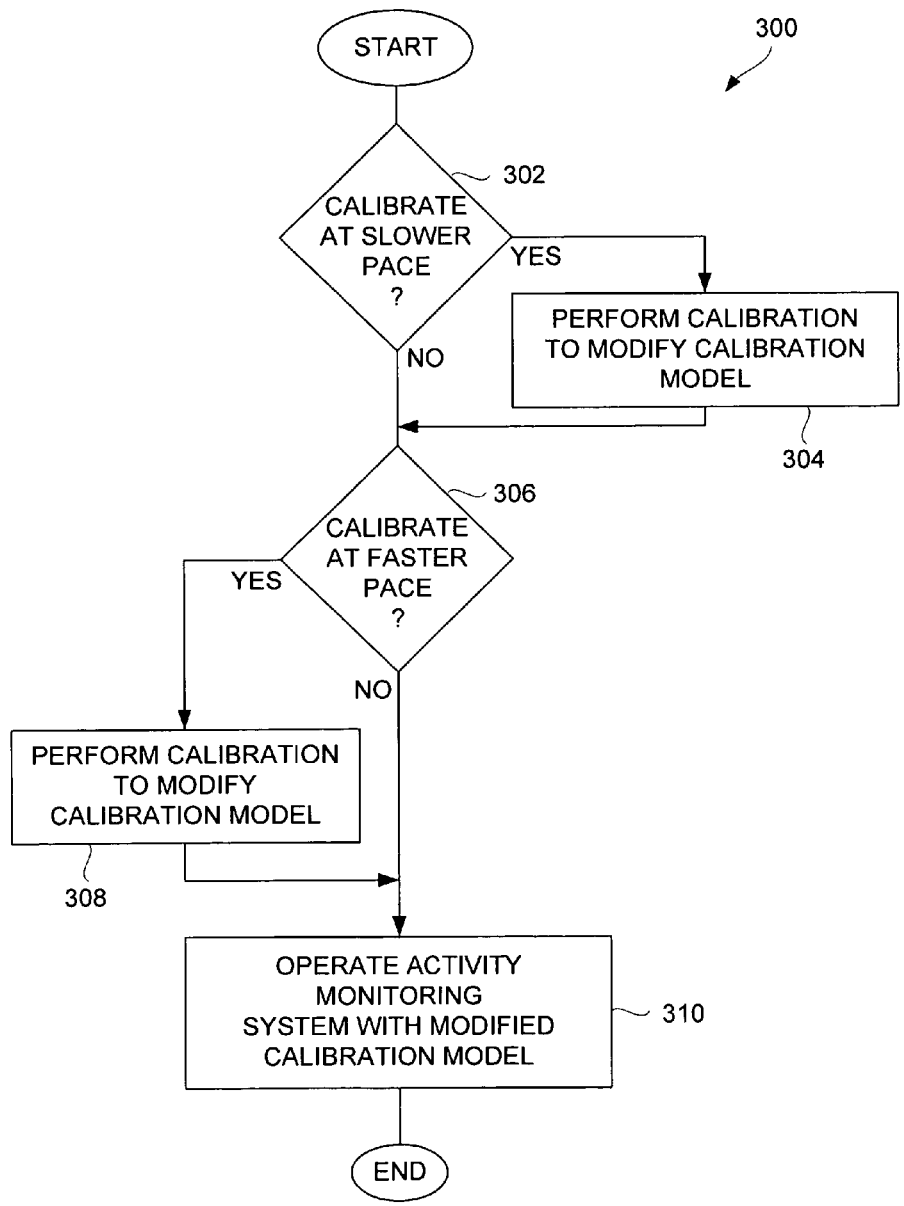
FIG. 3 is a flow diagram of a multi-speed calibration process according to one embodiment of the invention.

FIG. 3 is a flow diagram of a multi-speed calibration process 300 according to one embodiment of the invention. The multi-speed calibration process 300 is, for example, performed by an electronic device, such as the portable media device 102 illustrated in FIG. 1. More particularly, the multi-speed calibration process 300 can be performed by the activity monitoring system 200 illustrated in FIG. 2.

The multi-speed calibration process 300 begins with a decision 302. The decision 302 determines whether an activity monitoring system is to be calibrated at a slower pace. In this embodiment, the activity monitoring system can be calibrated at a slower pace as well as a faster pace. Typically, the pace pertains to walking or running that is performed by the user during a calibration process. When the decision 302 determines that the activity monitoring system is to be calibrated at a slower pace, calibration is performed 304 to modify a calibration model. The calibration model being modified is either a default calibration model or a previously determined calibration model.

Following the block 304, or following the decision 302 when the activity monitoring system is not to be calibrated at a slower pace, a decision 306 determines whether the activity monitoring system is to be calibrated at a faster pace. When the decision 306 determines that the activity monitoring system is to be calibrated at a faster pace, calibration is performed 308 to modify the calibration model.

Following the block 308, or following the decision 306 when the activity monitoring system is not to be calibrated at a faster pace, the activity monitoring system is operated 310 in accordance with the modified calibration model. Typically, following calibration, the calibration model is improved as compared to the calibration model prior to such additional calibration. As a result, the activity monitoring performed by the activity monitoring system is more accurate. For example, when the activity being monitored is walking or running, the activity monitoring system using the modified calibration model is able to more accurately determine characteristics of the walking or running, such as distance traveled, pace, etc.

The multi-speed calibration process 300 indicates that calibration can be performed at not only a slower pace but also a faster pace. The advantage of calibrating at a slower speed as well as a faster speed is that the calibration becomes more accurate and thus more reliable. However, it should be understood that in some embodiments, only one calibration need be performed. It should also be understood that in some embodiments, a calibration at one pace could be performed at one point in time, and calibration at another different pace could be performed sometime significantly later (e.g., day, week or months later).

Figure 4A:
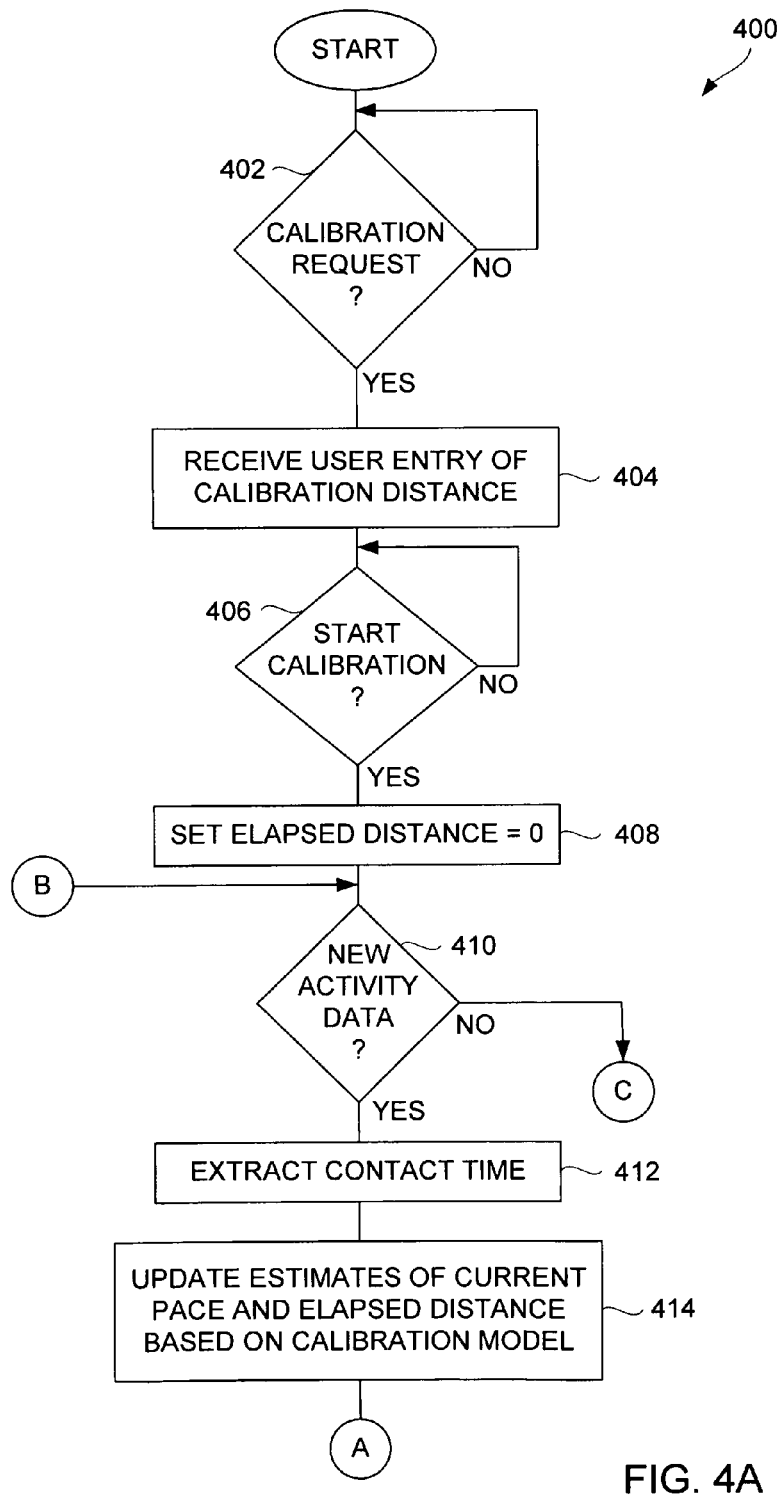
FIGS. 4A and 4B are flow diagrams of a calibration model improvement process according to one embodiment of the invention.
Figure 4B:
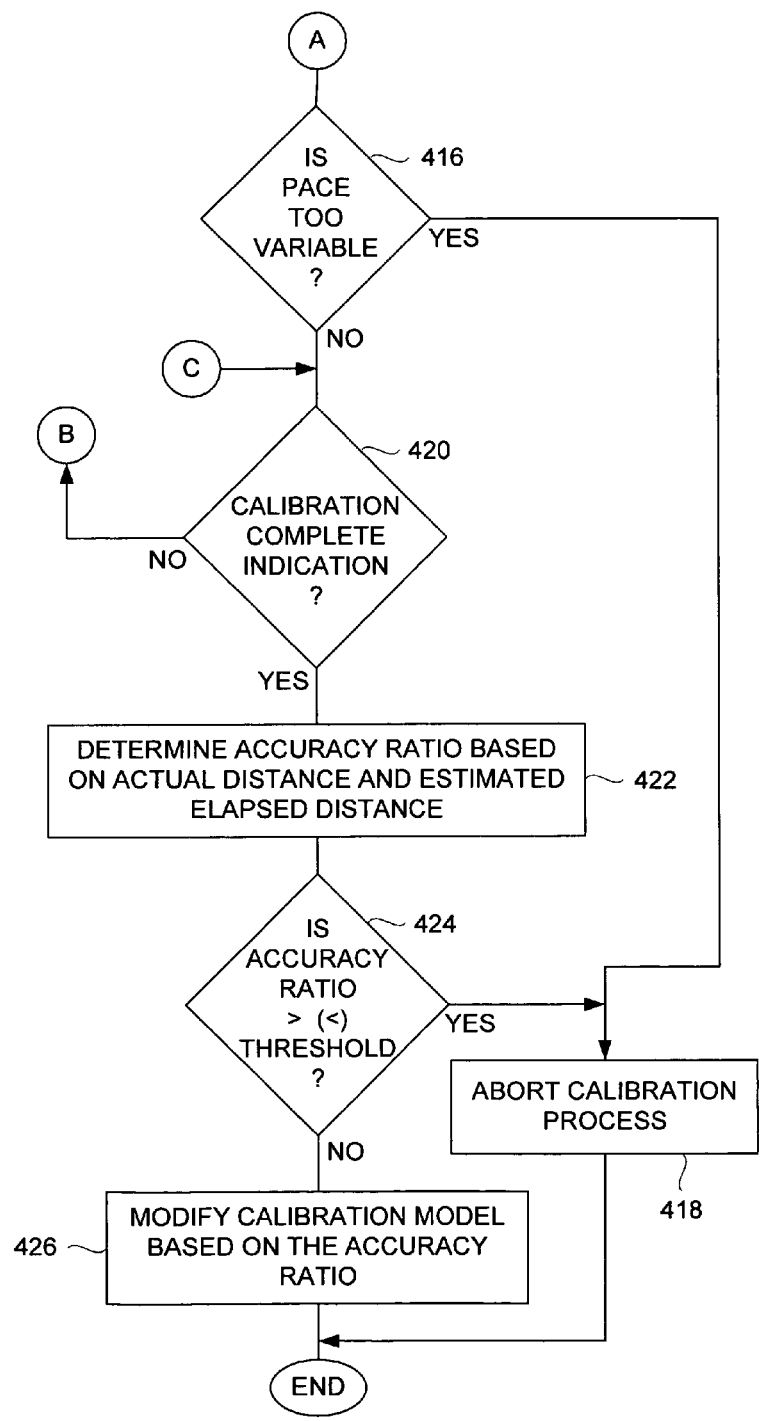

FIGS. 4A and 4B are flow diagrams of a calibration model improvement process 400 according to one embodiment of the invention. The calibration model improvement process 400 is, for example, performed by an electronic device, such as the portable media device 102 illustrated in FIG. 1. More particularly, the calibration model improvement process 400 can be performed by the activity monitoring system 200 illustrated in FIG. 2.

The calibration model improvement process 400 begins with a decision 402 that determines whether a calibration request has been received. In one embodiment, the calibration request can be initiated by a user of the electronic device. When the decision 402 determines that a calibration request has not been received, the calibration model improvement process 400 awaits such a request. On the other hand, when the decision 402 determines that a calibration request has been received, the calibration model improvement process 400 continues. In other words, the calibration model improvement process 400 is effectively invoked when the calibration request is received.

When the calibration model improvement process 400 continues, a user entry of a calibration distance is received 404. As an example, the user can interact with a user interface of the electronic device to enter or select a calibration distance (i.e., predetermined calibration distance). A decision 406 then determines whether calibration has been started. For example, the user of the electronic device can initiate calibration through user action, such as via the user interface of the electronic device. When the decision 406 determines that calibration has not been started, the calibration model improvement process 400 awaits start of the calibration.

Once the decision 406 determines that calibration is to be started, an elapsed distance is set 408 to zero. The elapsed distance is the distance that the user covers during the calibration process. The calibration process is typically associated with a walk or run by the user. Hence, the elapsed distance can thus be a distance to be run or walked during the calibration process.

Next, a decision 410 determines whether there is new activity data. The activity data, as noted above, with respect to FIG. 2, can be provided by an activity sensor that is separate from the electronic device (e.g., the portable media device 102). When the decision 410 determines that new activity data is present, a contact time is extracted 412 from the new activity data. Contact time is the time that the user's shoe is in contact with the ground as the user runs or walks. Using the contact time, estimates of current pace and elapsed distance can be updated 414 during the calibration process. The calibration model is used to acquire the current pace and elapsed distance from the new activity data (e.g., contact time).

A decision 416 then determines whether the pace for the calibration process, i.e., walk or run, is too varied. When the pace is determined to be too varied, then the calibration process is deemed unreliable. Hence, in such case, the calibration process is aborted 418. Alternatively, when the decision 416 determines that the pace is not too varied, a decision 420 determines whether a calibration complete indication has been received. In one embodiment, a user can interact with the electronic device to initiate a calibration complete indication. For example, the user can interact with the electronic device to signal that a predetermined calibration distance has been run or walked. In any case, when the decision 420 determines that a calibration complete indication has not been received, the calibration model improvement process 400 returns to repeat the decision 410 and subsequent blocks so that new activity data can be similarly processed.

On the other hand, when the decision 420 determines that a calibration complete indication has been received, an accuracy ratio is determined 422 based on actual distance and estimated elapsed distance. The actual distance is the distance the user ran or walked for the calibration process. Typically, the actual distance is the predetermined calibration distance that is chosen in block 404. For example, one common calibration distance is 400 meters, since such can be readily found at a 400 meters oval track. The estimated elapsed distance is the accumulated elapsed distances during the calibration process (block 414) as acquired using the electronic device.

Next, a decision 424 then determines whether the accuracy ratio is greater than (or less than) a threshold. In one implementation, the determination can determine whether the accuracy ratio is greater than a maximum threshold or less than a minimum threshold. These thresholds can be used to ensure that the accuracy ratio is not too excessive (e.g., too far from unity). A large or small accuracy ratio typically indicates that the calibration process was defective in some way. Hence, it is desirable to avoid using the data resulting from a calibration process that was defective. Hence, when the decision 424 determines that the accuracy ratio is greater than a threshold, the calibration process is aborted 418. Alternatively, when the decision 424 determines that the accuracy ratio is not greater than (less than) a threshold, then the calibration model is modified 426 based on the accuracy ratio. Following the block 426 as well as following the block 418, the calibration model improvement process 400 ends.

Although the calibration model improvement process 400 operates to receive a calibration request from a user to initiate the calibration process, it should be understood that in another embodiment, the activity data could be first captured and then subsequently a user could initiate the calibration process using the activity that was previously captured.

Figure 5:
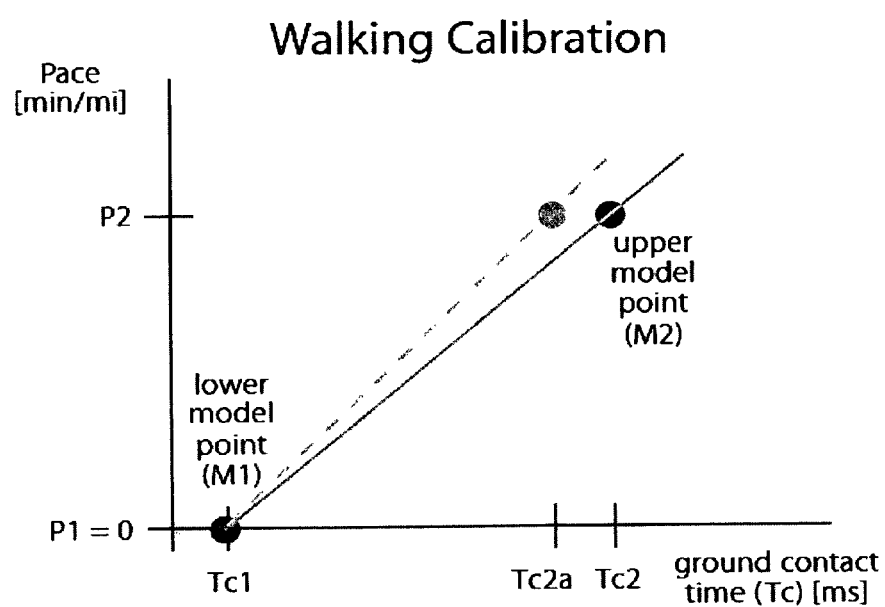
FIG. 5 illustrates a graph pertaining to walking calibration according to one embodiment of the invention.

FIG. 5 illustrates a graph pertaining to walking calibration according to one embodiment of the invention. The x-axis of the graph is for ground contact time (Tc) in milliseconds (ms), and the y-axis of the graph is for pace (P) in minutes/mile. The graph plots a calibration model. The calibration model is a line defined by two points, a lower model point (M1) and an upper model point (M2). The solid line represents an existing calibration model. The dotted line represents a modified calibration model that results following the walking calibration. In one embodiment, the modification (e.g., modifying 426) to the calibration model involves moving the upper model point (M2). The upper model point (M2) is moved left or right such that the ratio of the slope of the existing calibration line to slope of the modified calibration line is the same as the accuracy ratio (AR). The following equation is used to acquire the new upper model point (M2) for the calibration model:

$$Tc2a = (1 - AR) * Tc1 + AR * Tc2.$$

In effect, by moving the upper model point (M2) of the calibration model, the calibration pivots about the lower model point (M1). Although FIG. 5 pertains to walking calibration, the same calibration approach can be used for a running calibration. Preferably, the calibration lines for running and walking are separate lines.

In one embodiment, the user is recommended to perform a walking calibration and a running calibration. These different calibrations can be performed separately one after another on the same day or they can be performed many days apart. As an example, the walking calibration might move the upper model point (M2). In effect, by moving the upper model point (M2) of the calibration model, the calibration line pivots about the lower model point (M1).

Besides the calibration process illustrated in FIG. 5 in which one point of a line representing a calibration model is moved to render the calibration model more accurate, another calibration process can move more than one point (e.g., two points) of a line representing a calibration model.

Figure 6A:
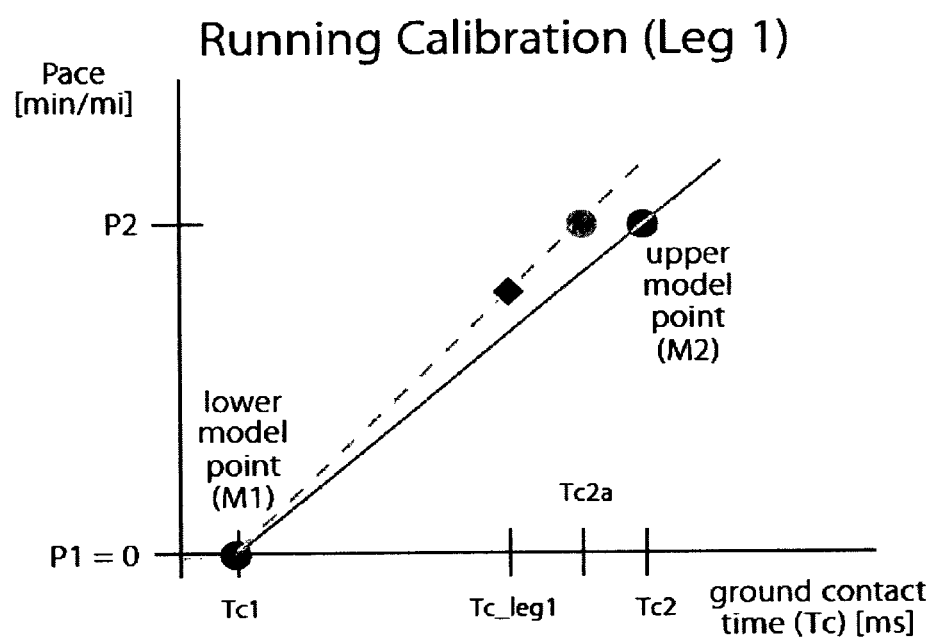
FIGS. 6A and 6B illustrate graphs pertaining to running calibration according to one embodiment of the invention.
Figure 6B:
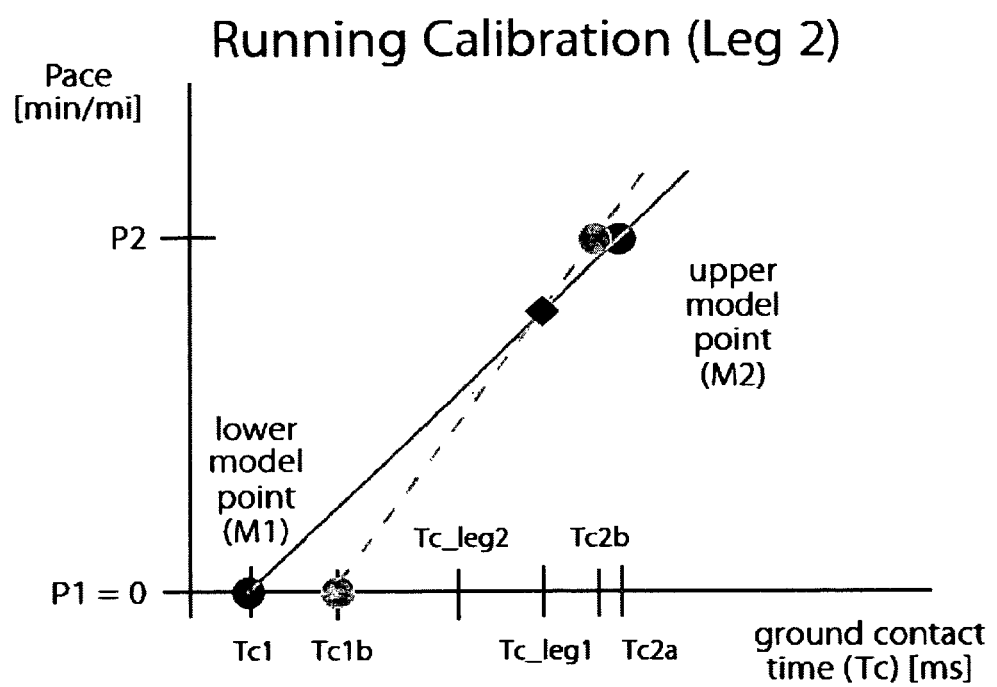

FIGS. 6A and 6B illustrate graphs pertaining to running calibration according to one embodiment of the invention. The running calibration is done in two stages or legs. The user will run at different paces during the different stages or legs. One of the paces is deemed a faster pace, and the other of the paces is deemed a slower pace.

In FIG. 6A, the graph illustrates calibration following a first stage or leg. The calibration process here is generally the same as that discussed above with reference to FIG. 5. Typically, this leg would correspond to a slower pace run. In addition, the average contact time (Tc_leg1) for the first stage or leg is stored.

In FIG. 6B, the graph illustrates calibration following a second stage or leg. In one embodiment, the modification (e.g., modifying 426) to the calibration model involves moving both the upper model point (M2) and the lower model point (M2). The average contact time (Tc_leg2) for the second stage or leg is determined from the user performance (i.e., activity data) of the second stage or leg of the calibration process as generally discussed above with regard to determining the average contact time (Tc_leg 1). If the average contact time (Tc_leg2) for the second stage or leg is too close to the average contact time (Tc_leg1) for the first stage or leg, then the average contact time (Tc_leg2) for the second stage or leg can be discarded and the calibration completed based on the calibration information for the first stage or leg.

On the other hand, if the average contact time (Tc_leg2) for the second stage or leg is not too close to the average contact time (Tc_leg1) for the first stage or leg, then the calibration process is completed using information from the second stage or leg. The lower model point (M1) is moved left or right such that the ratio of the slope of the existing calibration line to the slope of the modified calibration line is the same as the accuracy ratio (AR), while also insuring that the average contact time (Tc_leg1) for the first stage or leg remains on the modified calibration line. The following equations can be used to acquire the new lower model point (M1) for the calibration model:

$$Tc1b=(k*Tc\_leg1-AR*Tc\_leg2)/(k-AR), \text{ where}$$

$$k=(Tc\_leg2-Tc1)/(Tc\_leg1-Tc1).$$

In effect, by moving the lower model point (M1) of the calibration model, the calibration pivots about a point on the line that corresponds to the average contact time (Tc_leg1) for the first stage or leg. The calibration process can also check that Tc1b is within reasonable range limits for contact times. The reasonable range limits can be empirically determined from user population studies.

Once the new lower point (M1) is determined, the calibration process can determine a new upper point (M2) for the calibration model. The upper model point (M2) follows directly from the new lower point (M1) and the constraint that the "Tc_leg1" point be on the line. The following equations can be used to acquire the new upper model point (M2) for the calibration model:

$$Tc2b=(1-P2/P\_leg1)*Tc1b+P2/P\_leg1*Tc\_leg1,$$

where P_leg1 is the pace corresponding to Tc_leg1. Hence, calibration following a second stage or leg serves to move both the lower model point (M1) and the upper model point (M2).

Another aspect of the invention pertains to a graphical user interface. The graphical user interface can be provided to assist a user in performing a calibration process (i.e., fine-tuning) the accuracy of the activity monitoring system. The graphical user interface can be provided on a display device of a portable electronic device that provides the activity monitoring system.

Figure 7:
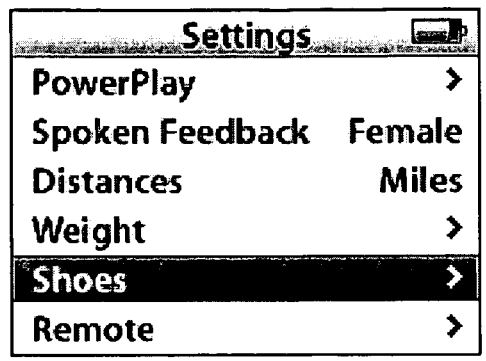
FIGS. 7-19 are exemplary screens that pertain to fine-tuning accuracy of an activity monitoring system.
Figure 8:
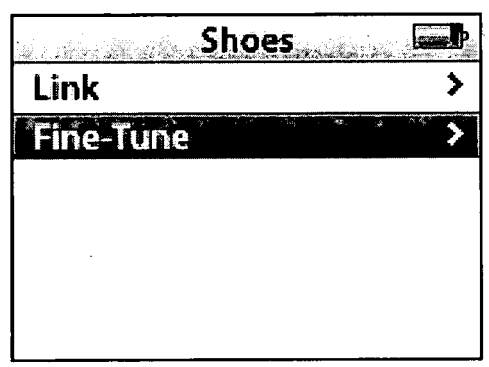
Figure 9:
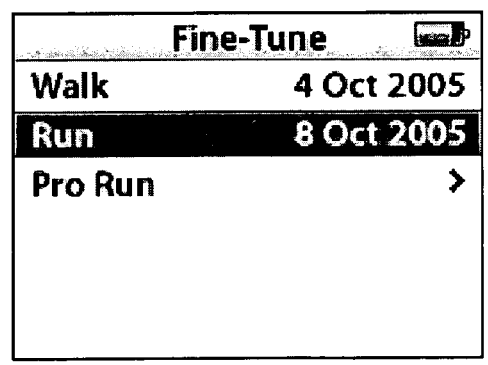
Figure 10:
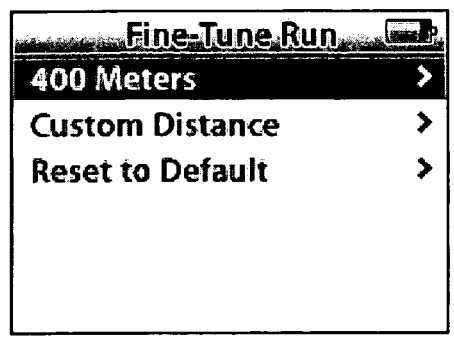
Figure 11:
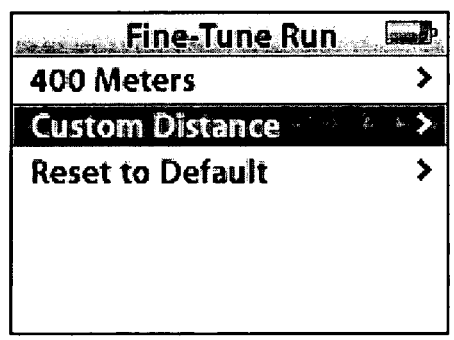
Figure 12:
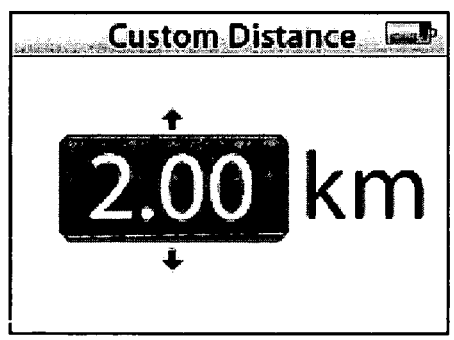

FIGS. 7-19 are exemplary screens that pertain to fine-tuning accuracy of an activity monitoring system. In FIG. 7, a settings screen is illustrated with the "Shoes" item highlighted. Upon selection of the "Shoes" item, a shoes screen such as illustrated in FIG. 8 can be displayed. As shown in FIG. 8, the "Fine-Tune" item is highlighted. When the "Fine-Tune" item is selected, a fine-tune status screen can be displayed such as illustrated in FIG. 9. In this example, the fine-tune status screen indicates that a walk-type fine-tune was performed on Oct. 4, 2005 and that a run-type fine-tune was performed on Oct. 8, 2005. The "Pro Run" item is shown in the fine-tune screen as not having yet been performed. When the "Run" item is selected from the fine-tune screen such as illustrated in FIG. 9, a fine-tune run screen such as illustrated in FIG. 10 can be displayed. From the fine-tune run screen, a user can select either a 400 meter run or a custom distance to be utilized for a fine-tune operation. Alternatively, the user could reset the fine-tune run data to its default data. When the fine-tune run screen is used to select the "Custom Distance" item as shown in FIG. 11, a custom distance screen such as illustrated in FIG. 12 can be displayed so that a user can enter a custom distance to be utilized with respect to the fine-tune run.

Figure 13:
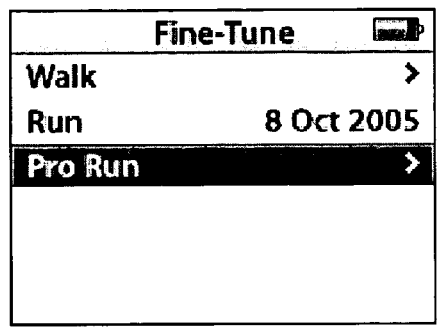
Figure 14:
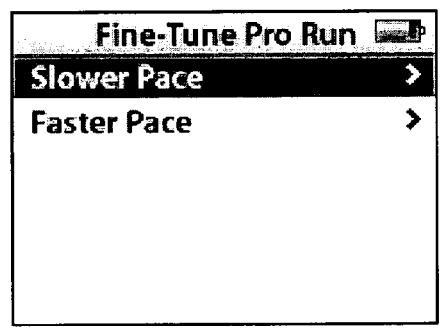
Figure 15:
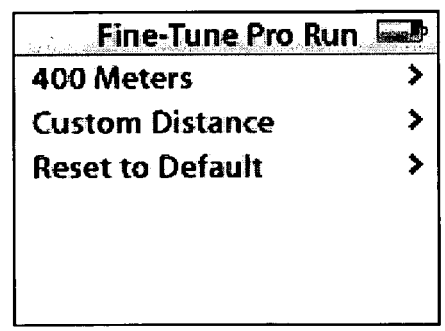

The fine-tune screen illustrated in FIG. 13 shows the "Pro Run" item being highlighted. When the "Pro Run" item is selected, a fine-tune pro run screen such as illustrated in FIG. 14 is displayed. The fine-tune pro run screen allows the user to elect to run at a slower pace or a faster pace for the fine-tune operation. Regardless of which pace is selected, a fine-tune pro run screen such as illustrated in FIG. 15 is displayed. The fine-tune pro run screen illustrated in FIG. 15 allows the user to select a predetermined distance, a custom distance or a reset operation.

Figure 16:
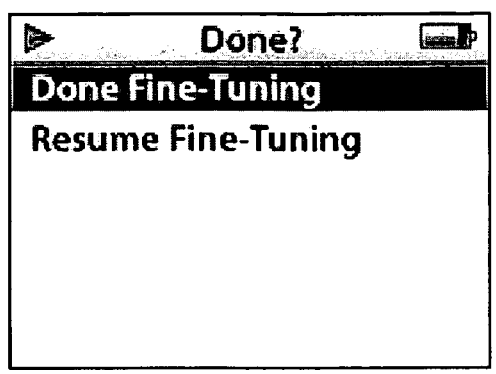
Figure 17:
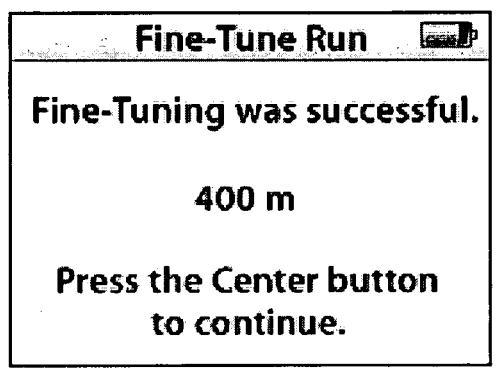
Figure 18:
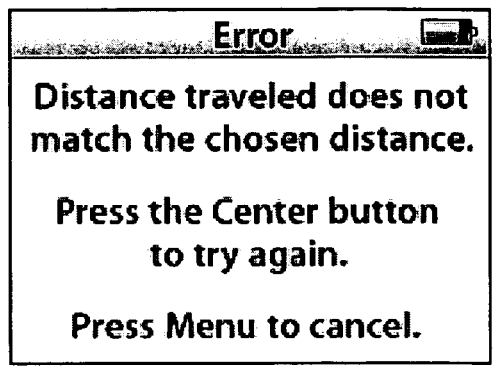
Figure 19:
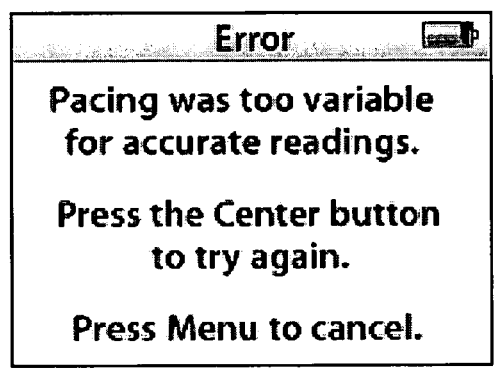

Once the fine-tune run has been specified, the user can be presented with a music selection screen and then a start screen. Once the user has indicated that they have started the fine-tune run, a workout status screen can be displayed as discussed above. When a pause request has been activated, such as by pressing a predetermined button, a fine-tune pause screen such as illustrated in FIG. 16 can be displayed. The fine-tune pause screen enables a user to end the fine-tuning or resume the fine-tuning. Regardless, when the fine-tune run has completed in a successful manner, a fine-tune run screen such as illustrated in FIG. 17 can be displayed. Alternatively, when the fine-tune run does not complete successfully, error screens such as illustrated in FIG. 18 or FIG. 19 can be displayed. The error screen shown in FIG. 18 indicates that the distance run by the user was not the chosen distance for the fine-tuning. FIG. 19 indicates that the user varied their pace too much during the fine-tuning run, which caused inaccuracies.

Although the calibration models illustrated in FIGS. 5, 6A and 6B utilize straight lines as calibration models, other calibration models could be utilized, such as calibration models that are curved or piecewise linear. In any case; in the event that a calibration model is unable to distinguish between multiple points, a stride time (Ts) can be utilized to discriminate between the multiple points on the calibration model. The stride time generally corresponds to the time period for a stride of a user (e.g., time period between successive heel contacts with the ground of a particular shoe).

Another aspect of the invention pertains to add to the storage of calibration data, such as a calibration model, at various locations within a system. For example, with respect to the sports monitoring system 100 illustrated in FIG. 1, the primary storage location for the calibration model is the portable media device 102. However, the calibration model can be stored at various other locations within the sports monitoring system 100. For example, the calibration model can be stored in the personal computer 110, the sports management server 118, the sports device 104, and/or the wireless interface accessory 106. There are different advantages for storing the calibration model at different parts of the sports monitoring system 100. Examples of the advantages for storing the calibration data at different parts of the sports monitoring system 100 are as follows. Since processing of activity data is normally performed at the portable media device 102, storage of the calibration model in the portable media device 102 allows for efficient processing. Storage of the calibration model in the wireless interface accessory 106 is useful because it renders the wireless interface accessory 106 portable with respect to different portable media devices. As an example, the wireless interface accessory 106 could be coupled to a different portable media device and operate properly without having to perform any recalibration operations. Similarly, storage of the calibration model in the sports device 104 should enable the sports device 104 to be fully portable between multiple different devices that might utilize the activity data captured by the sports device 104. Storage of the calibration model at the personal computer 110 can serve to provide backup storage for the calibration model as well as to permit processing of activity data at the personal computer. Storage of the calibration model at the sports management server 118 not only allows processing of activity data at the sports management server 118, but also facilitates gathering information on accurate calibration models for different groups of users. Advantageously, by having access to calibration models of numerous users, the sports monitoring system 100 could improve a default calibration model that is initially provided with the system. With a default calibration model that is sufficiently accurate, subsequent calibration by a user can be less necessary, simplified or eliminated.

According to another aspect of the invention, calibration models can be influenced by one or more other considerations. Examples of the other considerations are shoe type, gender, weight, fitness level, surface type, and inclination of surface. These other considerations can affect the calibration model, whether as a default or as a personalized calibration model.

In one embodiment, the system can detect the type of shoe being utilized by the user. The type of shoe can affect the calibration model, such as depending upon the stiffness of the shoe soles. Other characteristics of the shoe can also affect the calibration model. One approach to detecting the shoe stiffness is to include an electronic component within the shoe that can be sensed by another device, such as the portable media device or an accessory device. These sensors can, for example, include RFID tags, magnetic elements, or optical (e.g., infrared).

Figure 20:
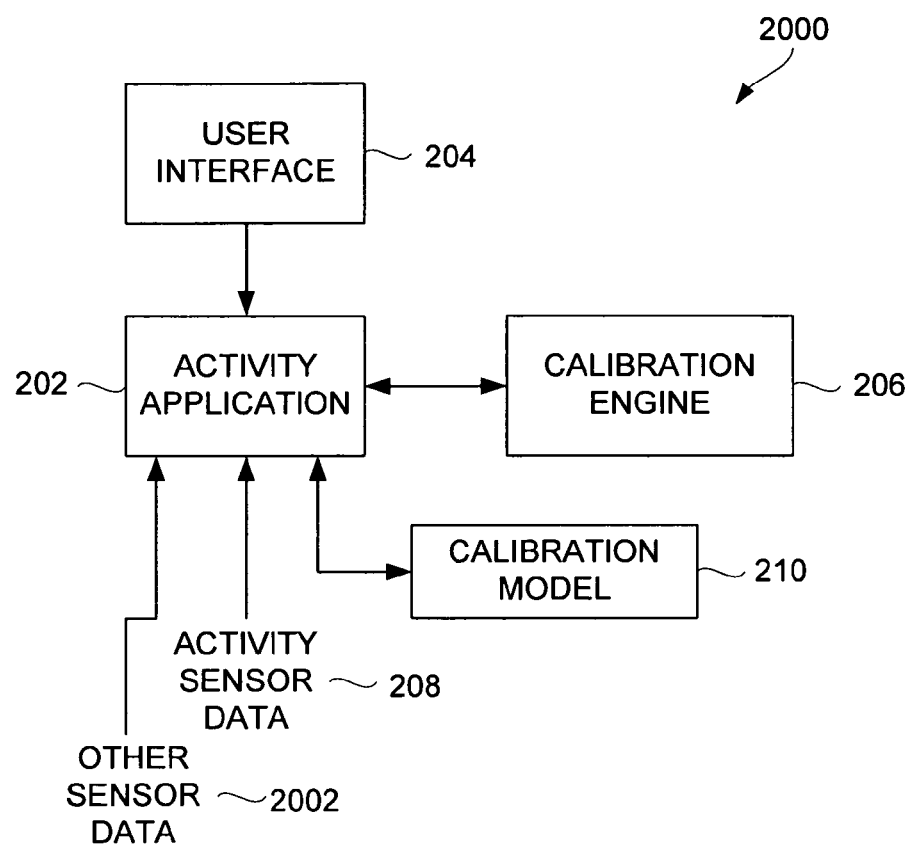
FIG. 20 is an activity monitoring system for an electronic device according to another embodiment of the invention.

FIG. 20 is an activity monitoring system 2000 for an electronic device according to another embodiment of the invention. The activity monitoring system 2000 is generally similar to the activity monitoring system 200 illustrated in FIG. 2 except that the activity application 202 further receives other sensor data 2002 in addition to the activity sensor data. The other sensor data 2002 can be used by the activity application 2002 when updating a calibration model 210. In one embodiment, the other sensor data 2002 provides data that pertains to shoe stiffness or other shoe characteristics (e.g., male or female type shoe). It should be noted that updating includes selection of an appropriate one of a plurality of calibration models, such as when a plurality of calibration models for different shoes are provided.

Another approach to determining shoe stiffness would be for the user to perform a predetermined action while wearing the shoe with the sports device 104. One type of predetermined action could pertain to the user jumping up and down. Besides these automatic approaches to determining shoe stiffness, in another embodiment, a user can manually interact with a user interface (e.g., such as a graphical user interface presented on a display of the user interface 204). As an example, the user interface can facilitate a user entering an indication of the type of shoe or its stiffness. As particular examples, a user could enter (i) a shoe model name or number, or (ii) a stiffness code provided on the shoe. As still another particular example, the user could navigate though a series of displayable images so as to select the shoe they are using by visual means.

In one embodiment, the system can detect the surface the user is running or walking on. For example, a sensor in the shoe, such as the sports sensor 104 or other sensor, could capture data that can signal the type of surface on which the user is running. For example, analysis of the captured data can be used to determine whether the user is running/walking indoors on a treadmill or running outdoors. As another example, analysis of the captured data can be used to determine whether the user is running/walking on hard surfaces (such as paved roads) or less hard surfaces (such as grass or athletic tracks). The captured data can thus be used to modify or select the calibration model for the type of surface.

Additionally, according to another aspect of the invention, a calibration model can be customized in view of calibration information available from a remote source. For example, the calibration model utilized by the portable media device 102 can be customized using calibration information or parameters available from the sports management server 118. For example, if the user of the portable media device 102 is also a user of the sports management server 118, the sports management server 118 may know certain characteristics, traits or other information about the user. For example, a user may have previously informed the sports management server 118 of one or more of shoe type, gender, weight, and fitness level. To the extent such information is useful to customize or improve a calibration model for the user, such information can be provided to the personal computer 110 and/or the portable media device 102 and utilized to provide an improved calibration model.

Another aspect of the invention pertains to performing calibration in a staged or deferred manner. With staged calibration, the calibration can be performed in parts. For example, a user may perform a walk calibration, which can lead to improvements to a default calibration model. Then, sometime later, the user can perform a run calibration at a slow pace that leads to further improvements to the calibration model. Still later, the user can perform a run calibration at a fast pace that can lead to still further improvements to the calibration model. Hence, as each stage of calibration is performed, the calibration model can be improved. However, none of the stages need be performed in any particular time or any particular order. Hence, the user is able to improve calibration as they have the time and interest to spend on calibration activities.

With deferred calibration, it is possible that the activity data that is transmitted by the sports device 104 to the wireless interface accessory 106 can be retained at any of a variety of different devices within the sports monitoring system 100. For example, the activity data could be stored at the personal computer 110 or the sports management server 118. By storing the activity data prior to its being processed with respect to a calibration model, such processing with respect to a calibration model can be performed sometime later when better and more accurate calibration models exist. This allows the devices of the sports monitoring system 100 to later reprocess activity data using improved calibration models. In other words, it allows after-the-fact processing of previously acquired activity data. This also allows analysis of a wide range of activity data across one or more calibration models.

Still another aspect of the invention pertains to merging different calibration models for the same user (e.g., same sports sensor 104). As noted above, calibration models can be stored at various locations within a system. These calibration models, if different, can be merged. For example, if a first calibration model resulted from a more recent slow run calibration and a second calibration model resulted from a more recent fast run calibration, then the first and second calibration models can be merged for improved accuracy. The merging of the calibration models can be performed from the calibration models themselves and/or the calibration data that yielded such calibration models.

During a calibration process, the user typically runs or walks a predetermined distance. It is important that the user's pace during the walk or run remain somewhat consistent. Hence, another aspect of the invention is for a portable media device to monitor the user's pace during the calibration walk or run. To the extent the user is not walking or running at a substantially consistent pace, the portable media device can alert the user through audio and/or visual feedback that they need to increase or decrease their pace to maintain the substantially consistent pace that is sought for the calibration process. Also, if during or at the conclusion of the calibration process the system recognizes that the pace of the calibration walk or run was not substantially consistent, the user can be notified that the calibration process was defective. Normally, the calibration data acquired during a defective calibration walk or run would be discarded.

The various aspects, embodiments, implementations or features of the invention can be used separately or in any combination.

The invention is preferably implemented by software, hardware or a combination of hardware and software. The invention can also be embodied as computer readable code on a computer readable medium. The computer readable medium is any data storage device that can store data which can thereafter be read by a computer system. Examples of the computer readable medium include read-only memory, random-access memory, CD-ROMs, DVDs, magnetic tape, optical data storage devices, and carrier waves. The computer readable medium can also be distributed over network-coupled computer systems so that the computer readable code is stored and executed in a distributed fashion.

The many features and advantages of the present invention are apparent from the written description. Further, since numerous modifications and changes will readily occur to those skilled in the art, the invention should not be limited to the exact construction and operation as illustrated and described. Hence, all suitable modifications and equivalents may be resorted to as falling within the scope of the invention.

What is claimed is:

1. A method of automatically updating a user's calibration model, the calibration model being used by a user activity monitoring system, the method comprising:

receiving from the user a selected activity type to be performed by the user for updating the user's calibration model;

receiving an indication of a calibration distance;

in response to receiving a calibration start indication:

receiving current user activity data corresponding to a user's current activity type;

determining if the user's current activity type is consistent with the selected activity type based upon the user activity data;

notifying the user to change the user's current activity type to the selected activity type when the user's current activity data indicates that the current activity type is not consistent with the selected activity type;

in response to a calibration stop indication:

estimating at teat a distance based on the received user activity data and an existing user calibration model;

determining an accuracy ratio based on the calibration distance and the estimated distance;

modifying the user's existing calibration model only if the accuracy ratio is within a range of acceptable accuracy ratios and the activity data is consistent; and using the user's modified calibration model to provide activity output data in accordance with the acceptable accuracy ratio.

2. The method as recited in claim 1, wherein the activity type is selected from a group that includes at least a walking type of activity, a jogging type of activity, a running type of activity.

3. The method as recited in claim 1, wherein the acceptable range of accuracy ratios is greater than a minimum accuracy ratio and less than a maximum accuracy ratio.

4. The method as recited in claim 1, wherein receiving the current user activity data comprises periodically receiving the activity data.

5. The method as recited in claim 1, wherein the estimate of at least the distance based on the received activity data and an existing calibration model further estimates a pace of the user based on the received activity data and the existing calibration model.

6. A non-transitory computer readable medium storing instructions for automatically updating a user calibration model used by an activity monitoring system during use activity, the instructions, when executed by one or more processors, are configured to cause the one or more processors to perform operations comprising:

receiving from the user a selected activity type to be performed by the user for updating the user calibration model;
receiving an indication of a calibration distance;
in response to receiving a calibration start indication:
  receiving current user activity data corresponding to a user's current activity type;
  determining if the user's current activity type is consistent with the selected activity type based upon the user activity data;
  notifying the user to change the user's current activity type to the selected activity type when the user's current activity data indicates that the current activity type is not consistent with the selected activity type;
in response to receiving a calibration stop indication:
  estimating at least a distance based on the received user activity data and an existing user calibration model;
  determining an accuracy ratio based on the calibration distance and the estimated distance;
  modifying the existing user calibration model only if the accuracy ratio is within a range of acceptable accuracy ratios and the user activity data is consistent; and
  using the modified user calibration model to provide activity output data in accordance with the acceptable accuracy ratio.

7. The computer readable medium as recited in claim 6, wherein the activity type is selected from a group that includes at least a walking type of activity, a jogging type of activity, a running type of activity.

8. The computer readable medium as recited in claim 6, wherein the acceptable range of accuracy ratios is greater than a minimum accuracy ratio and less than a maximum accuracy ratio.

9. A method for modifying an operation of an activity monitoring system associated with a user, the activity monitoring system having a processor and a user interface, the method comprising:
  receiving from the user a selected activity type to be performed by the user for the modifying an existing user calibration model;
  receiving a calibration request and a calibration distance from the user interface;
  receiving a calibration start indication;
  in response to receiving the calibration start indication:
    determining a current user activity type based upon current user activity data received from an activity sensor associated with the activity monitoring system;
    determining if the current user activity is consistent with the selected activity type;
    notifying the user to change the current user activity type to the selected activity type when the current user activity type is determined to not be consistent with the selected activity type;
    generating an estimated distance based on the received user activity data and an existing user calibration model;
    repeating the receiving user activity data from the activity sensor and generating the estimated distance until a calibration stop indication is received;
    determining an accuracy ratio based on the calibration distance and the estimated distance;
    modifying the existing user calibration model only if the accuracy ratio is within an acceptable range of accuracy ratios and the received user activity data is consistent; and
    modifying the operation of the activity monitoring system based on the modified user calibration model.

10. An auto-calibrating system for monitoring a user's activity, comprising:
an interface adapted to receive (i) an indication of a calibration distance from the user of the activity monitoring system and (ii) a user activity type, the calibration distance and user activity type used to update a user's calibration model; and
a processor coupled to the interface, the processor adapted to execute programming instructions that are configured to cause the processor to perform operations comprising:
receiving a calibration start indication;
in response to receiving the calibration start indication:
  receiving current user activity data corresponding to a user's current activity type;
  determining if the user's current activity type is consistent with a selected activity type; and
  notifying the user to change the user's current activity type to the selected activity type when the processor determines that the current activity type is not consistent with the selected activity type;
receiving a calibration stop indication; and
in response to receiving the calibration stop indication:
  estimating at least a distance based on the received user activity data and an existing user calibration model;
  determining an accuracy ratio based on the calibration distance and the estimated distance;
  modifying the user's existing calibration model only if the accuracy ratio is within a range of acceptable accuracy ratios and the activity data is consistent; and
  using the user's modified calibration model to provide activity output data in accordance with the acceptable accuracy ratio.

11. The auto-calibrating system as recited in claim 10, wherein the range of acceptable accuracy ratios is greater than a minimum accuracy ratio and less than a maximum accuracy ratio.

12. The auto-calibrating system as recited in claim 10, wherein the receiving activity data periodically receives the activity data.

13. The auto-calibrating system as recited in claim 10, wherein estimating the distance based on the received activity data and an existing calibration model further estimates a pace of the user based on the received activity data and the existing calibration model.

* * * * *

UNITED STATES PATENT AND TRADEMARK OFFICE
CERTIFICATE OF CORRECTION

PATENT NO. : 9,137,309 B2
APPLICATION NO. : 11/585721
DATED : September 15, 2015
INVENTOR(S) : John Meron Ananny and Nicholas Robert Kalayjian It is certified that error appears in the above-identified patent and that said Letters Patent is hereby corrected as shown below:

In the Claims

Column 14, Line 35; In Claim 1, delete "teat" and insert -- least --, therefor.

Column 14, Line 64; In Claim 6, delete "use" and insert -- user --, therefor.

Signed and Sealed this
Fifth Day of July, 2016

Michelle K. Lee
*Director of the United States Patent and Trademark Office*